US007683183B2

(12) United States Patent
Peters et al.

(10) Patent No.: US 7,683,183 B2
(45) Date of Patent: Mar. 23, 2010

(54) EMISSIVE MONOMERIC METAL COMPLEXES

(75) Inventors: Jonas C. Peters, Cambridge, MA (US); Alexander J. Miller, Pasadena, CA (US); Jillian Dempsey, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/888,210

(22) Filed: Jul. 30, 2007

(65) Prior Publication Data

US 2008/0064893 A1 Mar. 13, 2008

Related U.S. Application Data

(60) Provisional application No. 60/834,053, filed on Jul. 28, 2006.

(51) Int. Cl.
*C07F 15/00* (2006.01)
(52) U.S. Cl. .......................... 548/402; 556/21
(58) Field of Classification Search .................. 556/21; 548/402
See application file for complete search history.

(56) References Cited

U.S. PATENT DOCUMENTS

2007/0111026 A1 5/2007 Deaton et al.

OTHER PUBLICATIONS

Miller et al., Inorganic Chemistry, vol. 46, No. 18, pp. 7244-7246 (2007).*
Vlček Jr., Antonín, "The life and times of excited states of organometallic and coordination compounds," _Coordination Chemistry Reviews_, 200-202, 2000, pp. 933-977.
De Silva, A. Prasanna, et al., "Combining luminescence, coordination and electron transfer for signalling purposes," *Coordination Chemistry Reviews*, 205, 2000, pp. 41-57.
Cieśla, Pawel, et al., "Homogeneous photocatalysis by transition metal complexes in the environment," *Journal of Molecular Catalysis A Chemical*, 224, 2004, pp. 17-33.
Brown, Gilbert M., et al., "Homogeneous Catalysis of the Photoreduction of Water by Visible Light. Mediation by a Tris(2,2'-bipyridine)ruthenium(II)-Cobalt(II) Macrocycle System," *Journal of American Chemical Society*, 101:5, Feb. 28, 1979, pp. 1298-1300.
Ford, Peter C., et al., "Photoluminescence Properties of Multinuclear Copper(I) Compounds," *Chem. Rev.*, 99, 1999, pp. 3625-3647.
Horváth, Ottó "Photochemistry of copper (I) complexes," *Coordination Chemistry Reviews*, 135/136, 1994, pp. 303-324.
Balzani, Vincenzo, et al., "Luminescent and Redox-Active Polynuclear Transition Metal Complexes," *Chem. Rev.*, 96, 1996, pp. 759-833.
McMillin, David R., et al., "Photoprocesses of Copper Complexes That Bind to DNA," *Chem. Rev.*, 98, 1998, pp. 1201-1219.
Cuttell, Douglas G., et al., "Simple Cu(I) Complexes with Unprecedented Excited-State Lifetimes," *J. Am. Chem. Soc.*, vol. 124, No. 1, 2002, pp. 6-7.
Ziolo, Ronald F., et al., "The Photoluminescence of Phosphine Complexes of $d^{10}$ Metals," *Chemical Communications*, 1970, pp. 1124-1125.

(Continued)

*Primary Examiner*—Porfirio Nazario Gonzalez
(74) *Attorney, Agent, or Firm*—Christie, Parker & Hale, LLP

(57) ABSTRACT

Monomeric metal complexes having improved luminescence properties are provided. In one embodiment, a monomeric metal complex is represented by the formula $[PN]M(L)_2$. PN is an amidophosphine ligand, and M may be any metal capable of exhibiting luminescent properties, for example, a $d^{10}$ metal. L may be a tertiary phosphine. Alternatively, a second PN ligand or DPPE may take the place of both L ligands.

20 Claims, 17 Drawing Sheets
(16 of 17 Drawing Sheet(s) Filed in Color)

OTHER PUBLICATIONS

Kutal, Charles, "Spectroscopic and Photochemical Properties of $d^{10}$ Metal Complexes," *Coordination Chemistry Reviews*, 99, 1990, pp. 213-252.

Tsuboyama, Akira, et al., "Photophysical Properties of Highly Luminescent Copper(I) Halide Complexes Chelated with 1,2-Bis(diphenylphosphino)benzene," *Inorganic Chemistry*, vol. 46, No. 6, 2007, pp. 1992-2001.

Harkins, Seth B., et al, "A Highly Emissive $Cu_2N_2$ Diamond Core Complex Supported by a [PNP] Ligand," *J. Am. Chem. Soc.*, 127, 2005, pp. 2030-2031.

Harkins, Seth B., et al, "Amido-Bridged $Cu_2N_2$ Diamond Cores that Minimize Structural Reorganization and Facilitate Reversible Redox Behavior between a $Cu^1Cu^1$ and a Class III Delocalized $Cu^{1.5}Cu^{1.5}$ Species," *J. Am. Chem. Soc.*, 126, 2004, pp. 2885-2893.

Mankad, Neal P. et al., "Structrual Snapshots of a Flexible $Cu_2P_2$ Core that Accommodates the Oxidation States $Cu^1Cu^1$, $Cu^{1.5}Cu^{1.5}$, and $Cu^{II}Cu^{II}$", *J. Am. Chem. Soc.*, 127, 2005, pp. 16032-16033.

Liang, Lan-Chang, et al., "Amido Phosphine Complexes of Zinc," *Inorganic Chemistry*, vol. 42, No. 18, 2003, pp. 5471-5473.

Demas, J. N., et al., "The Measurement of Photoluminescence Quantum Yields, A Review," *The Journal of Physical Chemistry*, vol. 75, No. 8, Apr. 15, 1971, pp. 991-1024.

Scaltrito, Donald V., et al., "MLCT excited states of cuprous bis-phenanthroline coordination compounds," *Coordination Chemistry Reviews*, 208, 2000, pp. 243-266.

Kirchhoff, Jon R., et al., "Temperature Dependence of Luminescence from $Cu(NN)_2^+$ Systems in Fluid Solution. Evidence for the Participation of Two Excited States," *Inorg. Chem.*, 22, 1983, pp. 2380-2384.

Timpson, Cliff J., et al., "Influence of Solvent on the Spectroscopic Properties of Cyano Complexes of Ruthenium (II)," *J. Phys. Chem.*, 100, 1996, pp. 2915-2925.

Bargossi, Carlotta et al., "Recent developments in transition metal ion detection by luminescent chemosensors," *Coordination Chemistry Reviews*, 208 (2000) pp. 17-32.

Riegler, Jürgen et al., "Application of luminescent nanocrystals as labels for biological molecules," *Anal Bioanal Chem*, (2004) 379, pp. 913-919.

Wallace, William L. et al., "Electrogenerated Chemiluminescence. 35. Temperature Dependence of the ECL Efficiency of $Ru(bpy)_3^{2+}$ in Acetonitrile and Evidence for Very High Excited State Yields from Electron Transfer Reactions," *The Journal of Physical Chemistry*, vol. 83, No. 10, 1979, pp. 1350-1357.

DA RE, Ryan E. et al., "Molecular Spectroscopy of Uranium (IV) Bis(ketimido) Complexes. Rare Observation of Resonance-Enhanced Raman Scattering from Organoactinide Complexes and Evidence for Broken-Symmetry Excited States," *J. Am. Chem. Soc.*, 2005, 127, pp. 682-689.

University Science Books, Edited by Que, Jr., Lawrence, *Physical Methods in Bioinorganic Chemistry Spectroscopy and Magnetism*, Copyrighted 2000, pp. 25-27.

\* cited by examiner

EMISSIVE MONOMERIC METAL COMPLEXES

CROSS-REFERENCE TO RELATED APPLICATION(S)

This application claims priority to U.S. Provisional Application Ser. No. 60/834,053, filed on Jul. 28, 2006, the entire content of which is incorporated herein by reference.

FIELD OF THE INVENTION

The invention is directed to emissive monomeric metal complexes.

BACKGROUND OF THE INVENTION

Luminescent transition metal complexes have been widely studied for their use in biological imaging, photochemical catalysis, and light-driven fuel production. Conventionally, Pt and Ru based emitters have been used, but the high cost of such emitters has led to the investigation of Cu as a lower cost, biologically relevant replacement. To that end, the most thoroughly studied Cu emitters are monomers supported by modified polypyridine and phenanthroline ligands. However, these complexes suffer from low quantum efficiencies and short luminescence lifetimes.

In an effort to address the quantum efficiency and luminescence lifetime shortcomings of the polypyridine and phenanthroline supported Cu emitters, bulky bidentate phosphines using tertiary phosphines and substituted phenanthroline ligands in concert have been investigated. These complexes inhibit exciplex quenching, which provides longer lifetimes and improved quantum efficiency. The use of bulky diphosphine ligands in simple phosphine complexes of copper halides has also been researched. However, although these complexes can be highly emissive in the solid state in low temperature solvent glasses, they display only faint, short-lived emission in solution at ambient temperatures.

Recently, amide-bridged dicopper complexes, such as [(PNP)Cu]$_2$ (PNP$^-$=bis(2-(diisopropylphosphino)phenyl)amide) have been researched. These dimeric copper complexes possess both long lifetimes and highly efficient emission. However, the complex ligands required to produce such dimers are difficult to manipulate, which makes changing the properties of the dimer challenging.

SUMMARY OF THE INVENTION

In one embodiment of the present invention, a monomeric metal complex is represented by Formula 1.

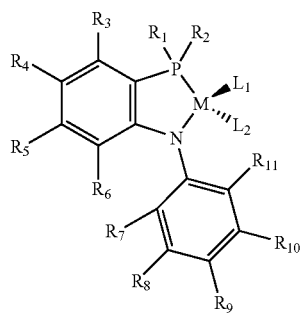

Formula I

As shown in Formula 1, M is bonded to an amidophosphine (PN) ligand and two additional ligands ($L_1$ and $L_2$). M may be any metal capable of producing emission characteristics, for example, M may be a d$^{10}$ metal. The PN ligand is represented by Formula 2.

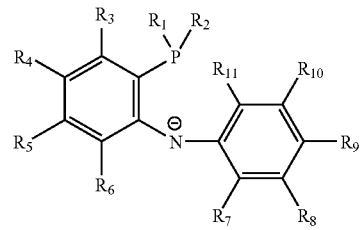

Formula 2 (PN Ligand)

In both Formulae 1 and 2, $R_1$ and $R_2$ may each independently be any hydrocarbon substituent. Also, each of $R_3$ through $R_{11}$ can be hydrogen or any other substituent suitable for substituting phenyl rings. The $L_1$ and $L_2$ ligands may each independently be a substituent represented by PX$_3$, where each X group may be any hydrocarbon substituent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features and advantages of the present invention will be better understood by reference to the following detailed description when considered in conjunction with the accompanying drawings in which.

DETAILED DESCRIPTION OF THE INVENTION

Figure 1:
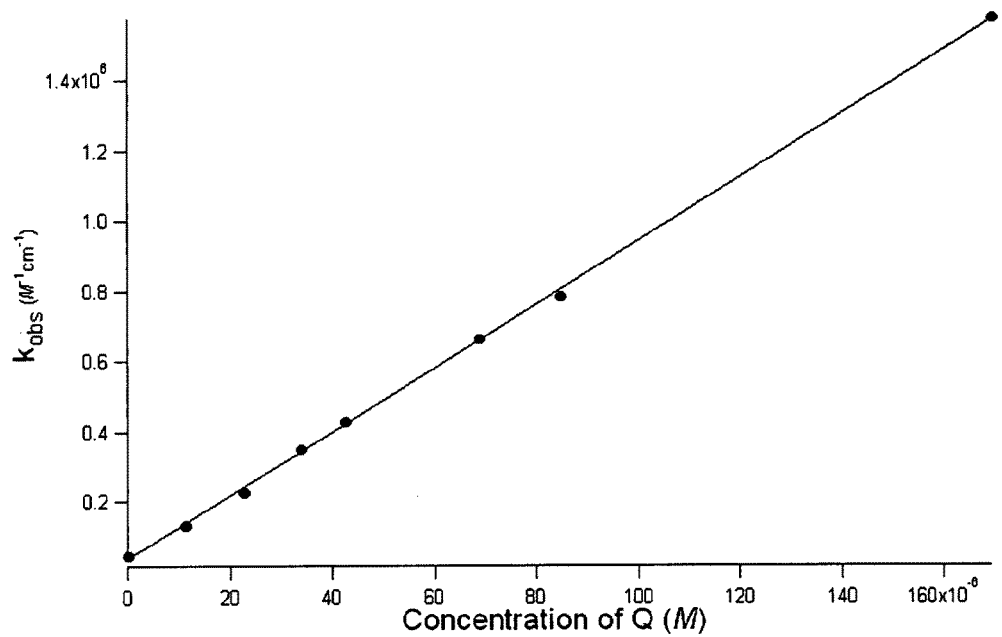
FIG. 1 is a Stem-Volmer plot of $k_{obs}$ vs. concentration of DCQ indicating the oxidative quenching of the compound prepared according to Example 2 with 2,6-dibenzoquinone (Q)

The present invention is directed to monomeric metal complexes having excellent emission and luminescence properties, including long lifetimes and good quantum efficiency. In addition to excellent luminescence properties, the inventive monomeric metal complexes are more cost-effective than previously investigated luminescent compounds, and have structures that are easily manipulable. Ease of manipulation is one important benefit of the inventive complexes because manipulation of the complex structure enables easy modification of the properties of the complex and easy tuning of the color and luminescence properties of the complex.

In one embodiment, a monomeric metal complex is selected from compounds represented by Formula 1.

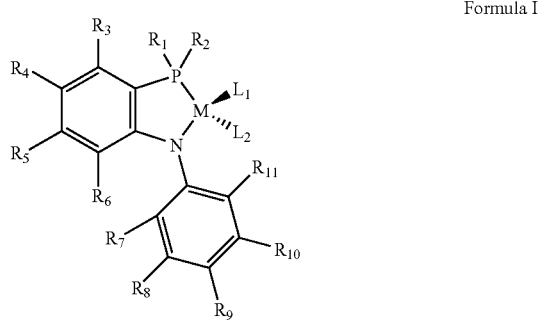

Formula I

As shown in Formula 1, M is bonded to an amidophosphine (PN) ligand and two additional ligands ($L_1$ and $L_2$). M may be any metal capable of producing emission characteristics. In one embodiment, for example, M is a $d^{10}$ metal. Nonlimiting examples of suitable metals for M include Cu, Ag and Zn. In one embodiment, for example, M is Cu, and these Cu complexes exhibit unusually long lifetimes (about 16 to about 150 μs), extremely high quantum efficiency (Φ ranging from 0.16 to about 0.70), and variable emission maxima ranging from about 500 to about 550 nm in benzene at 298K.

The PN ligand may be represented by Formula 2.

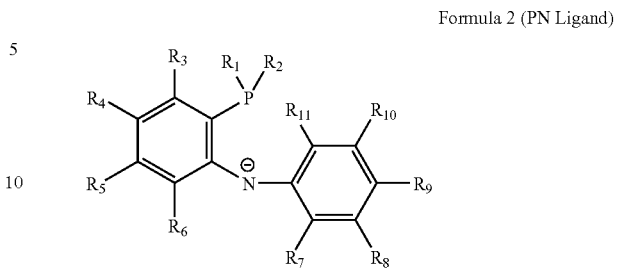

Formula 2 (PN Ligand)

In both Formulae 1 and 2, $R_1$ and $R_2$ can each independently be any hydrocarbon substituent, and the hydrocarbon substituents may be either substituted or unsubstituted. Nonlimiting examples of suitable hydrocarbon substituents include substituted and unsubstituted alkyl groups, substituted and unsubstituted alkenyl groups, substituted and unsubstituted alkynyl groups, substituted and unsubstituted aryl groups, substituted and unsubstituted heteroaryl groups, and the like. In one embodiment for example, each of $R_1$ and $R_2$ is an isopropyl group. In another embodiment, each of $R_1$ and $R_2$ is a phenyl group.

Each of $R_3$ through $R_{11}$ can be hydrogen or any other substituent. Substituents for substituting phenyl rings are well known, and any such known substituents may be used for $R_3$ through $R_{11}$. Nonlimiting examples of suitable substituents for $R_3$ through $R_{11}$ include hydrogen, halogens, hydroxyl groups, cyano groups, alkoxy groups, acyl groups, substituted or unsubstituted alkyl groups, substituted or unsubstituted alkenyl groups, substituted or unsubstituted alkynyl groups, substituted or unsubstituted aryl groups, substituted or unsubstituted heteroaryl groups, and the like. In one embodiment, at least one of $R_3$ through $R_{11}$, for example $R_5$, is selected from methyl groups and trihalo-substituted methyl groups, such as a trifluoro methyl group.

In addition, in another embodiment, one of $R_3$ through $R_6$ (for example $R_6$) and one of $R_7$ through $R_{11}$ (for example $R_7$) may combine to form a single bond between the phenyl rings, such that the emissive metal complex is represented by Formula 3.

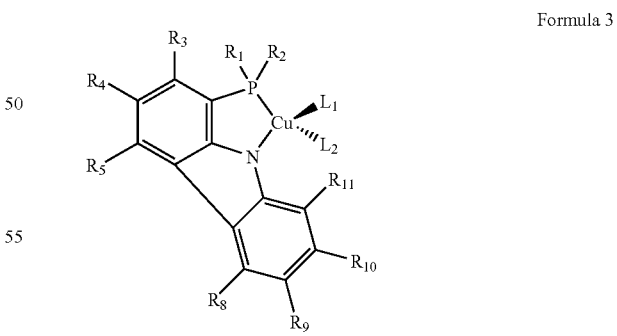

Formula 3

Substituting the phenyl rings with at least one substituent group, as discussed above, may enable fine tuning of the emission properties of the resulting complex. For example, emission efficiency may be tuned by including an electron donating or electron withdrawing group on the arene backbone of the PN ligand. Nonlimiting examples of such groups include methyl groups and trifluoromethyl groups.

According to one embodiment, the PN ligand may be prepared by nucleophilic attack of LiP$^i$Pr$_2$ ($^i$Pr=isopropyl) on fluorine-substituted diarylamine precursors. One nonlimiting example of such a fluorine-substituted diarylamine precursor is 1-fluoro-diphenylamine, which, after nucleophilic attack of LiP$^i$Pr$_2$, provides [PN]Li (shown in Reaction Scheme 1 below). A related PN ligand may be prepared having phenyl, rather than isopropyl, substituents at the P site, as noted above.

The L$_1$ and L$_2$ ligands may each independently be a substituent represented by PX$_3$, where each X group may be any hydrocarbon substituent. Nonlimiting examples of suitable hydrocarbon substituents for X include alkyl groups, alkenyl groups, alkynyl groups, aryl groups, heteroaryl groups, and the like. In one embodiment for example, each X group is a methyl or phenyl group, such that the emissive metal complex is represented by either Formula 4 or Formula 5.

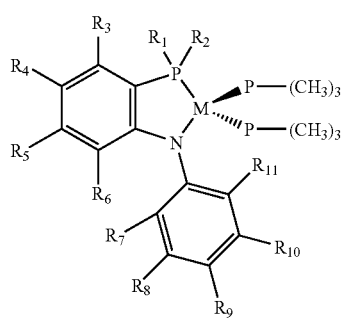

Formula 4

(X = methyl group)

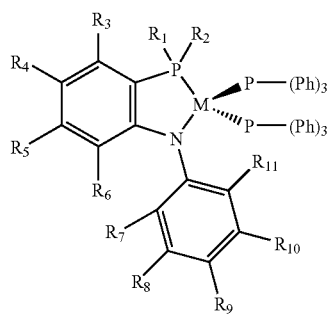

Formula 5

(X= phenyl group)

According to another embodiment of the present invention, the L$_1$ and L$_2$ ligands together comprise a single, second PN ligand, i.e. L$_1$+L$_2$=a PN ligand. According to this embodiment, the emissive metal complex is represented by Formula 6A.

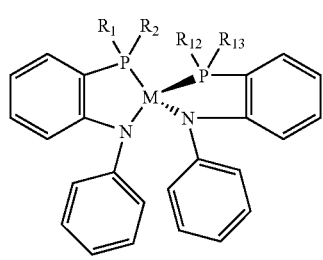

Formula 6A

In Formula 6A, each of the four phenyl rings are shown without their corresponding R groups for clarity. However, both PN ligands include phenyl rings with R groups as discussed above with respect to Formula 1. In addition, in Formula 6A, the R groups on the phenyl rings in the second PN ligand are the same as the R groups R$_3$ through R$_{11}$, discussed above in connection with Formula 1.

In another embodiment, the L$_1$ and L$_2$ ligands together comprise a single DPPE (1,2-(diisopropylphosphino)ethane) ligand, i.e. L$_1$+L$_2$=DPPE. According to this embodiment, the emissive metal complex is represented by Formula 6B.

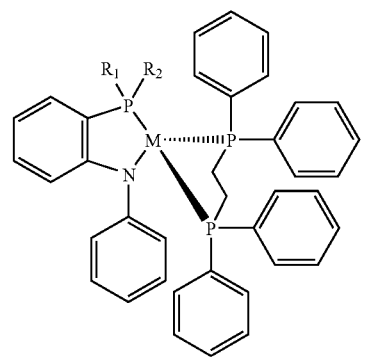

Formula 6B

In Formula 6B, the phenyl rings on the PN ligand are shown without their corresponding R groups for clarity. However, the PN ligand may include phenyl rings with R groups as discussed above with respect to Formula 1. In addition, any of the phenyl rings on the DPPE ligand may be substituted at any position with any suitable substituent. Any substituent suitable for the R$_3$ through R$_{11}$ groups on the PN ligand are also suitable for substituents on the phenyl rings of the DPPE ligand.

According to one embodiment of the present invention, a monomeric Cu complex may be synthesized according to the following Reaction Scheme 1. In Reaction Scheme 1, a simple PN ligand having isopropyl substituents at the P site is used. However, any other PN ligand may be used in Reaction Scheme 1. In addition, Reaction Scheme 1 depicts the synthesis of a monomeric Cu complex, but similar Reaction Schemes may be used to synthesize monomeric complexes of other metals, such as other d$^{10}$ metals (e.g., Zn and Ag).

Reaction Scheme 1

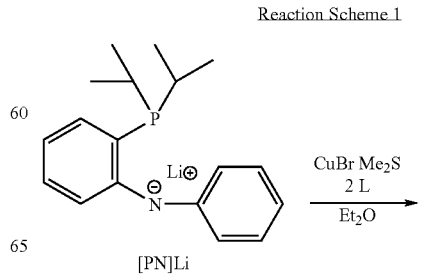

[PN]Li

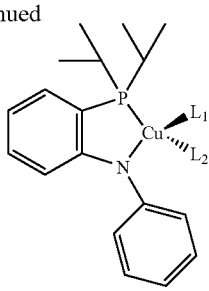

[PN]Cu[L]₂
L₁, L₂ = PR₃ or
L₁ + L₂ = diphenylphosphinoethane (DPPE)

[PN]Li, shown in Reaction Scheme 1, exhibits blue luminescence when irradiated with a UV lamp, and features an optical spectrum with transitions at 411 nm, 354 nm and 286 nm. As shown in Reaction Scheme 1, the [PN]Cu[L]₂ complex may be prepared by adding diethyl ether solutions of [PN]Li to a stirring suspension of CuBr.Me₂S and the appropriate tertiary phosphine. The resulting Cu complexes are bright yellow in color.

Cu complexes represented by Formulae 4, 5 and 6B may be synthesized according to Reaction Scheme 1. To prepare complexes with different ligands (L1 and L2), the proper tertiary phosphine (PR₃) is selected as 2 L. Specifically, to prepare the complex of Formula 4, L is P(CH₃)₃. To prepare the complex of Formula 5, L is P(Ph)₃. To prepare the complex of Formula 6B, 2 L is DPPE.

Also, the complex of Formula 3 may be prepared according to a reaction scheme similar to Reaction Scheme 1. In particular, the reaction scheme begins with a [PN]Li precursor in which the two phenyl rings are fused, as shown in Formula 3. The rings of the [PN]Li precursor may be fused by any suitable means, and in one embodiment the rings are fused via a Goldberg coupling. After preparing a [PN]Li precursor having fused phenyl rings, the compound represented by Formula 3 is produced according to Reaction Scheme 1.

To prepare complexes of other metals, for example Ag and Zn, the CuBr.Me₂S solution is replaced with a suitable solution for preparing complexes of the desired metal. For example, to prepare an Ag complex of Formula 5, AgOTF and diethyl ether are used. As another example, a Zn complex of Formula 6A may be prepared using ZnCl₂ and THF (tetrahydrofuran). More specific examples of the synthesis of various exemplary complexes of the invention are described in the below Examples.

EXAMPLES

The following Examples are presented for illustrative purposes only and are not to be construed as limiting the scope of the present invention. In the Examples, all manipulations were carried out using standard Schenk or glove-box techniques under a dinitrogen atmosphere. Unless otherwise noted, solvents were deoxygenated and dried by thorough sparging with $N_2$ followed by passage through an activated alumina column. Non-halogenated solvents were tested with a standard purple solution of sodium benzophenone ketyl in tetrahydrofuran in order to confirm effective oxygen and moisture removal. Deuterated solvents were degassed and stored over activated 3-Å molecular sieves prior to use. THF-$d_8$ was dried by passage over activated alumina and stored over activated sieves prior to use. LiP($^i$Pr)₂ was prepared according to know procedures. All other reagents were purchased from commercial vendors and used without further purification, unless explicitly stated otherwise. NMR spectra were recorded at ambient temperature on a Varian Mercury 300 MHz or Inova Automated 500 MHz spectrometer. $^1$H NMR chemical shifts were referenced to residual solvent. $^{31}$P NMR chemical shifts are reported relative to an external standard of 85% $H_3PO_4$. $^{19}$F NMR chemical shifts are reported relative to either a HCF₃ or C₆F₆ standard. UV-vis measurements were taken on a Varian Cary 50 Bio Spectrophotometer, using a quartz crystal cell with a Teflon stopper. Electrochemical analysis was performed on a CHI 600B Potentiostat/Galvanostat using a glassy carbon working electrode, a platinum wire auxiliary electrode, and a Ag/AgNO₃ (0.01 M) reference electrode filled with THF, with reference to Fc/Fc⁺ as an internal standard. X-ray diffraction studies were carried out on a Bruker Smart 1000 CCD diffractometer.

One precursor material used in the following Examples was 2-fluoro-diphenylamine, and was prepared as follows. In a glovebox, a 200 mL Teflon-stopped high-pressure flask was charged with Pd₂dba₃ (315 mg, 0.344 mmol; dba=dibenzylideneacetone), DPPF (275 mg, 0.688 mmol; DPPF=1,1'-bis(diphenylphosphino)ferrocene), NaO$^t$Bu (4.62 g, 48.16 mmol), and 80 mL toluene. The reaction flask was removed from the glovebox, and 1-bromo-2-fluorobenzene (3.74 mL, 34.4 mmol) and aniline (3.14 mL, 34.4 mmol) were added by syringe under $N_2$ counterflow. The mixture was heated in an oil bath at 100° C. overnight. After verifying consumption of starting materials by gas chromatography-mass spectrometry ("GC-MS") and $^{19}$F NMR, the mixture was cooled and filtered through a plug of silica, and washed with copious amounts of petroleum ether to yield a light yellow solution. The solvents were removed in vacuo, yielding the desired product as a pale orange oil (5.49 g, 85%). ($^1$H NMR (C₆D₆, 300 MHz): δ 7.15-6.95 (m, 3H, Ar—H), 6.89-6.65 (m, 4H, Ar—H), 6.5 (m, 2H, Ar—H), 5.36 (br, 1H, NH); $^{19}$F NMR (282 MHz): δ −132.5. HRMS (EI⁺) m/z calculated for C₁₂H₁₀FN: 187.0797. Found: 187.0796 [M⁺], 168.0947 [M-F]).

Another precursor material used in the following Examples was 2-fluoro-5-methyl-diphenylamine, and was prepared as follows. In a glovebox, a 200 mL high-pressure reaction vessel was charged with 30 mL toluene, Pd₂dba₃ (91.7 mg, 0.10 mmol), and 2-(dicyclohexylphosphino)biphenyl (140.2 mg, 0.40 mmol). The reaction flask was then removed from the box and stirred, with the dark red mixture turning more orange. As the reaction flask was stirring, 2-Fluoro-5-methylaniline (3.01 g, 24.05 mmol), iodobenzene (4.09 g, 20.04 mmol), and dry toluene were added to a 50 mL Schlenk flask, which was then boil-degassed. After subsequent cannula transfer of the organics into the high-pressure vessel, NaO$^t$Bu (2.70 g, 28.05 mmol) was added under $N_2$ counterflow, and the flask was sealed with a Teflon stopper. The mixture was heated to 110° C. for 20 hours, was allowed to cool to room temperature, was then filtered through a plug of silica, and washed with copious amounts of petroleum ether (about 250 mL). The solvent was removed, yielding an orange-brown oil. The crude product was purified by column chromatography on silica gel with petroleum ether eluent, yielding 2-fluoro-5-methyl-diphenylamine as a pale yellow oil (3.01 g, 70%). ($^1$H NMR (CDCl₃, 300 MHz): δ 7.31 (t, 2H), 7.12 (d, 3H), 7.00 (m, 2H), 6.64 (t, 1H), 6.75 (bs, 1H, NH), 2.27 (s, 3H, —CH$_3$). $^{19}$F NMR (282 MHz): δ −137.59 (s, 1F). HRMS (EI$^+$) m/z calcd. for C$_{13}$H$_{12}$FN: 201.0954. Found: 201.0957 [M$^+$]).

Example 1

Lithium-2-(diisopropylphosphino)diphenylamide (Starting Material)

A 1.6 M hexane solution of nBuLi (7.75 mL, 12.35 mmol) was added to a 200 mL Teflon-stopped flask charged with 20 mL of a light brown THF solution of 1-Fluoro-diphenylamine (2.20 g, 11.76 mmol). The mixture then turned orange and was stirred for 20 minutes. After concentration to 5 mL, a 50 mL solution of LiP(iPr)$_2$ (2.92 g, 23.52 mmol) in THF was added, and the vessel was removed from the glove-box and heated to 65° C. for 8 days, monitored by GC-MS and $^{19}$F NMR. The mixture turned dark green over time, and emitted blue luminescence under a UV lamp. When no remaining starting materials were detected spectroscopically, the mixture was brought back into the glove-box, and quenched with 5 mL EtOH. After addition of 40 mL petroleum ether, the reaction mixture was filtered through celite, and the solvents were removed in vacuo. As it was concentrated, the oily residue formed large sticky bubbles, and the mixture was repeatedly treated with diethyl ether and then re-concentrated to control the bubbling. The residual oil was extracted with petroleum ether, and filtered through a plug of silica. Removal of solvents left a brown oil that solidified when left at ambient temperatures overnight, and was determined to be about 80% [PN]H by NMR, with an unknown phosphine-containing product as an impurity. Addition of nBuLi (7.35 mL, 11.76 mmol) to a stirring solution of the brown solids resulted in immediate precipitation of the compound represented by Formula 7 (below), which was isolated on a sintered glass frit, and washed with copious amounts of petroleum ether before being collected as a spectroscopically pure, thermally unstable off-white powder (2.15 g, 64%). ($^1$H NMR (300 MHz, THF-d$^8$): δ 7.04 (m, 1H, Ar—H), 6.88 (m, 3H, Ar—H), 6.73 (m, 3H, Ar—H), 6.26 (t, 1H, Ar—H), 6.12 (t, 1H, Ar—H), 2.02 (m, 2H, CH(CH$_3$)$_2$), 1.11, (q, 6H, CH(CH$_3$)$_2$), 0.98 (q, 6H, CH(CH$_3$)$_2$). $^{31}$P NMR (120 MHz): δ −6.03 (q, 1P). HRMS (EI$^+$) m/z calculated for C$_{18}$H$_{24}$NP ([PN]H): 285.1646. Found: 285.1637 [M$^+$], 243.1072 [M-$^i$Pr], 200.0424 [M-2$^i$Pr]).

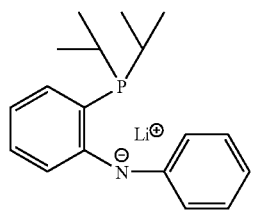

Formula 7

Example 2

[PN]Cu(PPh$_3$)$_2$

A diethyl ether solution (about 3 mL) of CuBr.Me$_2$S and PPh$_3$ were cooled to −35° C. The PPh$_3$-containing solution was added to the CuBr.Me$_2$S suspension and the mixture was stirred and protected from the light with aluminum foil. After 5 minutes, a cooled (−35° C.) diethyl ether solution of the compound prepared according to Example 1 was added slowly to the reaction mixture, and the solution turned bright yellow immediately. After 2 hours of stirring, the mixture was green-yellow, and the solvent was removed in vacuo. Extraction with benzene, followed by filtration through celite, yielded a bright yellow solution, which was lyophilized, affording a spectroscopically pure compound according to Formula 8 (below) as a yellow powder. X-Ray quality crystals were grown from vapor diffusion of a solution of the resulting compound in diethyl ether with petroleum ether. ($^1$H NMR (C$_6$D$_6$, 300 MHz): δ 7.3 (m, 30H, P(C$_6$H$_5$)$_3$), 7.02 (t, 2H, Ar—H), 6.92 (t, 3H, Ar—H), 6.79 (t, 1H, Ar—H), 6.72 (t, 1H, Ar—H), 6.59 (t, 1H, Ar—H), 6.17 (t, 1H, Ar—H), 2.26 (sept., 2H, CH(CH$_3$)$_2$), 1.08 (dd, 6H, CH(CH$_3$)$_2$), 0.99 (dd, 6H, CH(CH$_3$)$_2$). $^{13}$C NMR (75 MHz): δ 166.41, 158.39, 136.03 (d, J$_{PC}$=12.6 Hz), 134.61 (d, J$_{PC}$=16.9 Hz), 133.34, 132.43, 129.81, 129.76, 129.14 (d, J$_{PC}$=8.3 Hz), 128.93, 126.05, 119.70, 113.40 (d, J$_{PC}$=156 Hz), 23.85 (d, J$_{PC}$=12.31 Hz), 20.22 (d, J$_{PC}$=10.87 Hz), 19.02 (d, J$_{PC}$=3.0 Hz). $^{31}$P NMR (120 MHz): δ −1.2 (br, 2P), −3.7 (br, 1P). Anal. calcd. for C$_{54}$H$_{53}$CuNP$_3$ C, 74.34; H, 6.12; N, 1.61; Found: C, 74.31; H, 5.94; N, 1.60).

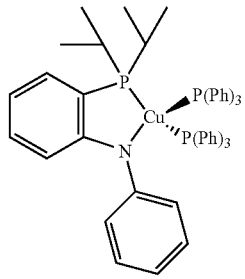

Formula 8

Example 3

[PN]Cu(PMe$_3$)$_2$

A diethyl ether solution (about 3 mL) of CuBr.Me$_2$S and P(CH$_3$)$_3$ were cooled to −35° C. The P(CH$_3$)$_3$-containing solution was added to the CuBr.Me$_2$S suspension and the mixture was stirred and protected from the light with aluminum foil. After 5 minutes, a cooled (−35° C.) diethyl ether solution of the compound prepared according to Example 1 was added slowly to the reaction mixture, and the solution turned bright yellow immediately. After 2 hours of stirring, the mixture was green-yellow, and the solvent was removed in vacuo. Extraction with benzene, followed by filtration through celite, yielded a bright yellow solution, which was lyophilized, affording a spectroscopically pure compound according to Formula 9 (below) as a yellow powder. X-Ray quality crystals were grown from a vapor diffusion of a diethyl ether solution of the resulting compound with petroleum ether. ($^1$H NMR (C$_6$D$_6$, 300 MHz.): δ 7.72 (q, 1H, Ar—H), 7.4 (m, 2H, Ar—H), 7.29 (t, 2H, Ar—H), 7.2-7.0 (m, 2H, Ar—H), 6.78 (tt, 1H, Ar—H), 6.54 (t, 1H, Ar—H), 1.95 (sept., 2H, CH(CH$_3$)$_2$), 1.10 (q, 6H, CH(CH$_3$)$_2$), 1.00 (q, 6H, CH(CH$_3$)$_2$), 0.85 (br. 18H, P(CH$_3$)$_3$). $^{13}$C NMR (125 MHz): δ 163.40, 158.20, 131.80, 130.65, 128.79, 128.19, 121.20, 117.63 (d, J$_{PC}$=34.9 Hz), 114.95, 114.07 (dd, J$_{PC}$=478.5 Hz, 3.7 Hz), 22.45 (d, J$_{PC}$8.8 Hz), 19.63 (d, J$_{PC}$=11.6 Hz), 18.41 (d, J$_{PC}$=3.3 Hz), 16.63 (d, J$_{PC}$=13.0 Hz).$^{31}$P NMR (120 MHz): δ 7.0 (br, 1P, [PN]), −46.3 (br, 2P, P(CH$_3$)$_3$). Anal. calcd. for C$_{24}$H$_{41}$CuNP$_3$ C, 57.64; H, 8.26; N, 2.80; Found: C, 57.61; H, 8.00; N, 2.84).

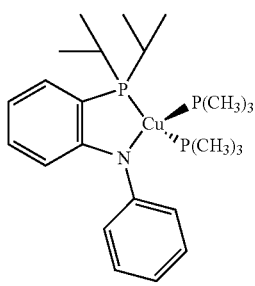

Formula 9

Example 4

[PN]CuDPPE

A diethyl ether solution (about 3 mL) of CuBr.Me$_2$S and DPPE (1,2-bis(diphenylphosphino)ethane) were cooled to −35° C. The DPPE-containing solution was added to the CuBr.Me$_2$S suspension and the mixture was stirred and protected from the light with aluminum foil. After 5 minutes, a cooled (−35° C.) diethyl ether solution of the compound prepared according to Example 1 was added slowly to the reaction mixture, and the solution turned bright yellow immediately. After 2 hours of stirring, the mixture was green-yellow, and the solvent was removed in vacuo. Extraction with benzene, followed by filtration through celite, yielded a bright yellow solution, which was lyophilized, affording a spectroscopically pure compound according to Formula 10 (below) as a yellow powder. Crystals used for X-Ray diffraction were grown from vapor diffusion of petroleum ether and a solution of the resulting product in THF. ($^1$H NMR (C$_6$D$_6$, 300 Mhz,): δ 7.65 (q, 2H, Ar—H), 7.44 (m, 8H, DPPE), 7.2-7.1 (m, 2H, Ar—H), 7.02 (d, 12H, DPPE), 6.9 (m, 3H, Ar—H), 6.55 (m, 2H, Ar—H), 2.18 (t, 4H, DPPE), 2.08 (sept., 2H, CH(CH$_3$)$_2$), 1.15 (q, 6H, CH(CH$_3$)$_2$), 0.89 (q, 6H, CH(CH$_3$)$_2$). $^{13}$C NMR (125 MHz): δ 159.27, 136.06, 133.82 (t, J$_{PC}$=8.1 Hz), 133.18, 131.53, 129.26, 129.09 (t, J$_{PC}$=4.3 Hz), 124.15, 117.03, 114.20 (dd, J$_{PC}$=571.3 Hz, 4.7 Hz), 68.16 (THF), 27.36 (td J$_{PC}$=17.1 Hz, 5.5 Hz), 26.16 (THF), 23.09 (d, J$_{PC}$=11.9 Hz), 19.89 (d, J$_{PC}$=11.1 Hz), 17.97. $^{31}$P NMR (120 Mhz): δ 8.7 (br, 1P, [PN]), −1.4 (br 2P, DPPE). Anal. calcd. for C$_{44}$H$_{47}$CuNP$_3$ C, 70.81; H, 6.35; N, 1.88; Found: C, 70.52; H, 6.46; N, 1.60).

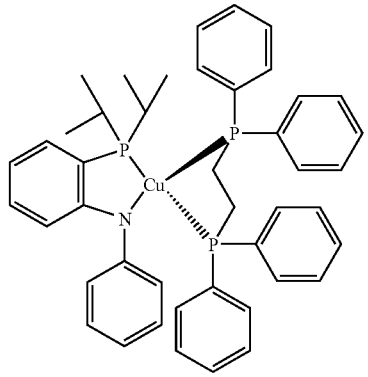

Formula 10

Example 5

[$^{Me}$PN]Li (Starting Material)

A 10 mL THF solution of 2-fluoro-5-methyldiphenylamine (1.452 g, 5.19 mmol) was cooled to −35° C. and added to a 100 mL high pressure flask. To this vessel was added a 1.6 M solution of nBuLi in hexane (3.41 mL, 5.45 mmol), dropwise with stirring. The clear colorless solution turned yellow, then orange, as it was warmed to room temperature, after which it was stirred for 2 hours. A 10 mL THF solution of LiP(iPr)$_2$ (1.611 g, 12.99 mmol) was added slowly to the mixture, and the vessel was sealed with a Teflon stopper, removed from the glovebox, and heated to 80° C. for 7 days. After this time, a GC-MS trace showed complete consumption of the starting material and growth of one other peak corresponding to the product. The flask was brought back into the glovebox, and the reaction was quenched with 5 mL EtOH, resulting in a pale green color, before removal of solvents. Filtration of the residue through silica, washing with copious amounts of petroleum ether, followed by removal of solvents in vacuo and another filtration through celite, yielded [$^{Me}$PN]Li as a mixture with another phosphorous-containing product (80% by 31P NMR integration). Addition of nBuLi (3.41 mL, 5.45 mmol) to a cooled (−35° C.) solution of this crude product in a solution of 10 mL petroleum ether resulted in immediate precipitation of beige solids. The mixture was stirred for 2.5 hrs before collecting the solids on a frit, and washing with 60 mL petroleum ether, affording pure [$^{Me}$PN]Li, a complex according to the following Formula 11. ($^1$H NMR (THF-d$^8$, 300 Mhz): δ 6.7-6.9 (m, 6H), 6.25 (t, 1H), 5.98 (d, 1H), 1.96-2.06 (m, 5H, Ar—CH$_3$, CH(CH$_3$)$_2$), 1.10 (dd, 6H), 0.95 (d, 6H). $^{31}$P NMR (120 MHz): δ −7.07 (m, 1H). HRMS (EI$^+$) m/z calcd. for C$_{19}$H$_{26}$NP: 299.1805. Found: 299.1803 [M$^+$], 257.1387 [M-$^i$Pr], 214.0860 [M-2$^i$Pr]).

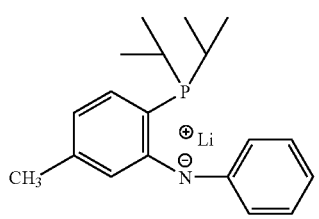

Formula 11

Example 6

[$^{CF3}$PN]Li (Starting Material)

In the glovebox, 1-Fluoro-4-trifluoromethyl-diphenylamine (1.94 g, 7.63 mmol) was dissolved in 20 mL THF, and added to a 200 mL Teflon-stopped glass vessel equipped with a stirbar. The vessel was cooled to −78° C., at which point a 1.6 M hexane solution of nBuLi (4.8 mL, 7.71 mmol) was added dropwise by syringe. The reaction mixture was allowed to warm while stirring for 30 minutes, during which time the solution darkened from pale orange to a darker orange-brown. At this point, a 10 mL THF solution of LiP(iPr)$_2$ (1.90 g, 15.33 mmol) was added to the reaction mixture, and the vessel was heated to 70° C. for 4 days, while monitoring the reaction for completion by GC-MS and $^{31}$P NMR. The reaction mixture, which had darkened to a red-brown, emitted yellow luminescence under a UV lamp. The vessel was cooled to room temperature, and was brought into the glovebox. The mixture was then quenched with 10 mL EtOH, and 10 mL of petroleum ether were added, yielding a golden-brown solution. The solvents were removed in vacuo. The oily residue was treated with 10 mL of diethyl ether, which was subsequently removed under reduced pressure; this procedure was repeated as necessary to reduce bubbling. The residue was extracted with petroleum ether, filtered through celite, and concentrated to a brown oil, which was left under dynamic vacuum overnight. The residue contained a mixture of [$^{CF3}$PN]H (about 85-90%) and one unknown P-containing side-product (δ +4 ppm). Crude [$^{CF3}$PN]H was dissolved in 20 mL of petroleum ether, added to a 100 mL round-bottom flask, and cooled to −35° C. A 1.6 M hexane solution of nBuLi (4.8 mL, 7.71 mmol) was then added dropwise by syringe, yielding a beige precipitate. The flask was warmed to room temperature and stirred overnight, at which point the solids were collected on a sintered glass frit, and washed with 40 mL petroleum ether, yielding spectroscopically pure [$^{CF3}$PN]Li (1.61 g, 59%), having the following Formula 12. ($^1$H NMR (THF-d$^8$, 300 MHz): δ 7.15 (d, 1H), 7.05-6.94 (m, 3H), 6.82 (dd, 2H), 6.45 (t, 1H), 6.24 (dd, 2H), 2.09 (sept, 2H, CH(CH$_3$)$_2$), 1.14 (q, 6H, CH(CH$_3$)$_2$), 1.00 (q, 6H, CH(CH$_3$)$_2$). $^{31}$P NMR: δ −6.6 (br q, 1P). $^{19}$F NMR: δ −60.5 (s, 3F). HRMS (EI$^+$) m/z calcd. for C$_{19}$H$_{23}$F$_3$NP: 353.1520. Found: 353.1506 [M$^+$], 311.1105 [M-$^i$Pr], 268.0594 [M-2$^i$Pr], 235.0692 [M-($^i$Pr)$_2$P]).

Formula 12

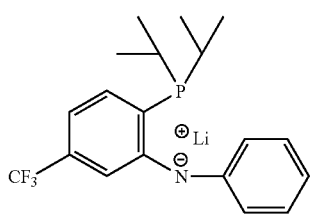

Example 7

[$^{Me}$PN]Cu(PPh$_3$)$_2$

Diethyl ether solutions of the compound prepared according to Example 5 (67.7 mg, 0.222 mmol), CuBr.Me$_2$S (45.6 mg, 0.222 mmol), and PPh$_3$ (116.3 mg, 0.444 mmol) were cooled to −35° C. PPh$_3$ was added to the cold suspension of CuBr.Me$_2$S while stirring, and the scintillation vial was covered with aluminum foil. After 5 minutes the compound prepared according to Example 5 was added slowly, and the reaction mixture was stirred for 2.5 hrs. After removal of solvent in vacuo, the residue was extracted with benzene, filtered through celite, and lyophilized, yielding [$^{Me}$PN]Cu (PPh$_3$)$_2$ (represented by Formula 13 below) in a quantitative yield as a yellow powder. X-Ray quality crystals were grown from a diethyl ether solution of the resulting product layered with petroleum ether and cooled to −30° C. ($^1$H NMR (C$_6$H$_6$, 300 MHz): δ 7.48-7.35 (m, 12H, P(C$_6$H$_5$)$_3$), 7.26 (d, Ar—H), 7.2-7.1 (m), 7.08-7.0 (m, 18H, P(C$_6$H$_5$)$_3$), 6.86 (t, 1H, Ar—H), 6.42 (d, 1H, Ar—H), 2.11 (s, 3H, [CH3PN]), 2.06 (sept, 2H, CH(CH$_3$)$_2$), 1.1-0.94 (m, 12H, CH(CH$_3$)$_2$). $^{13}$C NMR (75 MHz): δ 166.54, 158.34, 141.69, 135.80 (d, J$_{PC}$=12.0 Hz), 134.18 (d, J$_{PC}$=17.2 Hz), 132.98, 129.51, 128.87 (d, J$_{PC}$=8.3 Hz), 125.88, 119.35, 114.05 (dd, J$_{PC}$=75.3 Hz, 4.9 Hz), 23.51 (d, J$_{PC}$=13.1 Hz), 22.15, 19.92 (d, J$_{PC}$=11.2 Hz), 18.67 (d, J$_{PC}$=3.7 Hz). $^{31}$P NMR (120 MHz): δ 1.1 (2P), −3.9 (1P). Anal. calcd. for C$_{55}$H$_{55}$CuNP$_3$ C, 74.52; H, 6.25; N, 1.58. Found: C, 74.42; H, 6.45; N, 1.57).

Formula 13

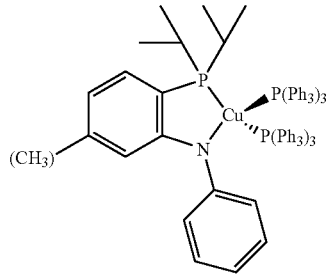

Example 8

[$^{CF3}$PN]Cu(PPh$_3$)$_2$

Diethyl ether solutions of the compound prepared according to Example 6 (97.8 mg, 0.273 mmol), CuBr.Me$_2$S (56.0 mg, 0.273 mmol), and PPh$_3$ (142.9 mg, 0.545 mmol) were cooled in scintillation vials to −35° C. PPh$_3$ solution was added to the slurry of CuBr.Me$_2$S before the vial was covered with aluminum foil and stirred for 5 minutes. The compound prepared according to Example 6 was slowly added to the slurry via pipette, which immediately resulted in a clear yellow solution. The reaction was stirred for 2 hr, at which point the solvents were removed in vacuo. The residues were extracted with benzene, and filtered through celite, yielding a bright yellow solution. The benzene was removed by lyophilization overnight, affording a spectroscopically pure yellow powder of [$^{CF3}$PN]Cu(PPh$_3$)$_2$ (represented by Formula 14 below) (254.6 mg, 99%). X-Ray quality crystals were grown from a cooled (−30° C.) layering of petroleum ether upon a diethyl ether solution of the resulting product. ($^1$H NMR (C$_6$D$_6$, 300 Mhz): δ 7.65 (d, 1H, [PN]Ar—h), 7.4 (m, 12H, P(C$_6$H$_5$)$_3$), 7.29 (d, 2H, [PN]Ar—H), 7.08 (t, 3H, [PN] Ar—h), 7.0 (m, 18 H, P(C$_6$H$_5$)$_3$), 6.83 (t, 1H, [PN]Ar—H), 6.76 (d, 1H, [PN]Ar—H), 1.933 (sept., 2H, CH(CH$_3$)$_2$), 0.977 (dd, 6H, CH(CH$_3$)$_2$), 0.873 (dd, 6H, CH(CH$_3$)$_2$). $^{13}$C NMR (125 MHz): δ 135.64 (d, J$_{PC}$=15.6 Hz), 134.54 (d, J$_{PC}$=17.09), 133.35, 129.59, 129.97 (d, J$_{PC}$=0.9 Hz), 129.20 (d, J$_{PC}$=8.3 Hz), 128.92 (d, J$_{PC}$=0.4 Hz), 125.42, 120.57, 109.41, 106.95, 23.86 (d, J$_{PC}$=12.4 Hz), 20.11 (d, J$_{PC}$=11.1 Hz), 18.91 (d, J$_{PC}$=3.1 Hz). $^{31}$P NMR (120 MHz): δ 0.19 (br, 2P, P(C$_6$H$_5$)$_3$), −3.98 (br, 1P, [PN]). 19 F NMR (470 MHz):

−63.4 (3F). Anal. calcd. for $C_{55}H_{52}CuF_3NP_3$ C, 70.24; H, 5.57; N, 1.49. Found: C, 70.10; H, 5.84; N, 1.45).

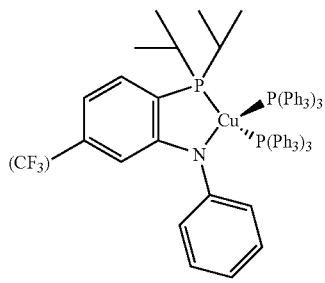

Example 9

$[PN]Ag(PPh_3)_2$

A 20 mL scintillation vial protected from the light was charged with AgOTf and 3 mL diethyl ether. To the stirring solution was added a diethyl ether solution of $PPh_3$, and five minutes subsequently was added a solution of the compound prepared according to Example 1. After 2 hours, the reaction mixture was filtered, and the bright yellow solution was dried in vacuo. The resulting product was $[PN]Ag(PPh_3)_2$ (represented by the following Formula 15). Analytically pure crystals were grown from a THF solution layered with petroleum ethers, and cooled to −30° C. ($^1$H NMR ($C_6D_6$, 300 MHz): δ 7.71 (t, 1H, Ar—H), 7.49 (d, 2H, Ar—H), 7.38 (m, 12H, $P(C_6H_5)_3$), 7.2-7.1 (m, 4H, Ar—H), 7.05 (m, 18H, $P(C_6H_5)_3$), 6.77 (t, 1H, Ar—H), 6.55 (t, 1H, Ar—H), 2.02 (sept., 2H, $CH(CH_3)_2$), 1.08 (q, 6H, $CH(CH_3)_2$), 0.93 (q, 6H, $CH(CH_3)_2$). $^{13}$C NMR (75 MHz): δ 159.2, 135.49 (d, $J_{PC}$=12.9 Hz), 134.70 (d, $J_{PC}$=17.5 Hz), 133.58, 131.82, 130.02, 129.70, 129.24 (d, $J_{PC}$=8.59 Hz), 123.67, 116.88, 113.43 (d, $J_{PC}$=33.2 Hz), 114.04 (d, $J_{PC}$=342.2 Hz), 23.92 (d, $J_{PC}$=7.44 Hz), 20.48 (d, $J_{PC}$=12.31), 19.23 (d, $J_{PC}$=4.87 Hz). $^{31}$P NMR (120 MHz): δ 7.7 (1P), 5.5 (2P). Anal. Calcd. for $C_{54}H_{53}AgNP_3$ C, 70.74; H, 5.83; N, 1.53. Found: C, 70.67; H, 6.03; N, 1.51).

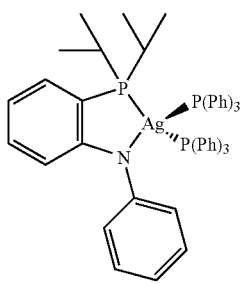

Example 10

$[PN]_2Zn$

To a THF solution of $ZnCl_2$ (16.0 mg, 0.1174 mmol in 3 mL) chilled to −35° C. in a scintillation vial, was added 2 equivalents of the compound prepared according to Example 1 (68.4 mg, 0.235 mmol) in 5 mL cold THF solution, while stirring. The mixture was allowed to warm to room temperature while stirring for 3 hours. The golden reaction solution was then filtered through celite, dried by evaporation, and extracted with diethyl ether. Filtration through celite, followed by washing with 2 mL ether, yielded a golden yellow solution that was layered with petroleum ether and cooled to −30° C., affording golden crystals of analytically pure $[PN]_2Zn$ (represented by Formula 16 below). ($^1$H NMR ($C_6D_6$, 300 MHz): δ 7.2-7.1 (m, 4H), 7.08-6.9 (m, 10H), 6.61 (t, 2H), 6.25 (m, 2H), 2.36 (sept, 4H, $CH(CH_3)_2$), 1.28 (q, 6H, $CH(CH_3)_2$), 1.18 (q, 6H, $CH(CH_3)_2$), 1.02 (q, 6H, $CH(CH_3)_2$), 0.36 (q, 6H, $CH(CH_3)_2$). $^{13}$C NMR: δ 162.87 (t, $J_{PC}$=7.8 Hz), 154.62, 132.77 (d, $J_{PC}$=6.4 Hz), 129.87, 124.62, 120.69, 115.14, 113.26, 107.85 (t, $J_{PC}$=21.2 Hz), 23.46 (t, $J_{PC}$=7.4 Hz), 21.19 (t, $J_{PC}$=10.5 Hz), 19.35 (t, $J_{PC}$=3.6 Hz), 18.86 (t, $J_{PC}$=4.1 Hz), 17.96 (t, br), 16.69 (s, br). $^{31}$P NMR (120 MHz): δ −12.23 (2P). Anal calcd. for $C_{36}H_{46}ZnN_2P_2$ C, 68.19; H, 7.31; N, 4.42. Found: C, 68.47; H, 7.50; N, 4.04).

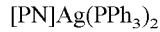

Formula 16

Testing and Measurement

The compounds prepared according to Examples 1 through 10 were subjected to the following testing and measurement procedures.

X-Ray Crystallography

X-ray quality crystals were grown for each complex. The crystals were mounted on a glass fiber with Paratone-N oil. Structures were determined using direct methods with standard Fourier techniques using the Bruker AXS software package. In some cases, Patterson maps were used in place of the direct methods procedure.

Lifetime Measurements

A solution of analyte in diethyl ether or benzene was prepared in a nitrogen filled glovebox. The quartz cuvettes (1 cm pathlength) were charged with this solution, and sealed with a Teflon stopper. Absorption spectra were acquired both before and after measurements to ensure the sample was not photodegrading. Generally, there was an insignificant amount (<1%) of photodecomposition under the experimental conditions, although there was more pronounced degradation under prolonged irradiation. Luminescence lifetime measurements were carried out using 8 ns pulses (at a repetition rate of 10 Hz) from a Nd:YAG laser pumped OPO (Quanta Ray Pro, Spectra Physics). The luminescence was dispersed through a monochromator (Instruments SA DH-10) onto a photomultiplier tube (PMT) (Hamamatsu R928). The PMT current was amplified and recorded with a transient digitizer (Lecroy 9354A). Measurements were performed at 298 K with two cuvettes of analyte solution, with excitation at $\lambda_{ex}$=430 nm for the compounds prepared according to Examples 2, 3, 4, 7 and 8, excitation at $\lambda_{ex}$=440 nm for the compound prepared according to Example 9, and excitation at $\lambda_{ex}$=310 nm for the compounds prepared according to

Examples 1 and 10. Emission was collected at the wavelength, $\lambda_{em}$, specified in Table 1, below. The emission decay was averaged over at least 500 laser pulses, and fit to an exponential function from which $k_{obs}$ and $\tau$ were determined. For the compounds prepared according to Examples 3 and 8, the short-lived portion of the bi-exponential function was below the response time of the amplifier, and is approximated at <10 ns. The Zn complex prepared according to Example 6 also had a lifetime that was too short to quantify, and so is estimated simply as <10 ns.

TABLE 1

Data for Excited State Lifetime Measurements.

| Sample | $\lambda_{em}$ (nm) | $k_{obs}$ (s$^{-1}$) | Lifetime ($\tau$) ($\mu$s) |
|---|---|---|---|
| 223 $\mu$M Example 1 in Et$_2$O | 480 | 8.64 × 10$^7$ | 0.012 (1) |
| 40.3 $\mu$M Example 2 in C$_6$H$_6$ | 504 | 4.94 × 10$^4$ | 20.2 (1) |
| 80.0 $\mu$M Example 3 in C$_6$H$_6$ | 503 | (a) 4.44 × 10$^4$ (b) n/a | 22.3 (7) <10 ns |
| 77.7 $\mu$M Example 4 in C$_6$H$_6$ | 533 | 6.15 × 10$^4$ | 16.3 (3) |
| 98.1 $\mu$M Example 9 in C$_6$H$_6$* | 517 | 8.76 × 10$^6$ | 0.125 (5) |
| 49.6 $\mu$M Example 7 in C$_6$H$_6$ | 504 | 1.50 × 10$^5$ | 6.7 (1) |
| 57.4 $\mu$M Example 8 in C$_6$H$_6$* | 555 | (a) 6.76 × 10$^3$ (b) n/a | 150 (3) <10 ns |

*= Sample was excited at 440 nm.

Oxidative Luminescence Quenching

Samples were prepared from two stock solutions: 34 $\mu$M Example 2 in C$_6$H$_6$, and a mixture of 34 $\mu$M Example 2 and 339 $\mu$M 2,6-dichlorobenzoquinone (DCQ). Using cuvettes with Teflon-separated 25 mL bulbs, solutions of varying concentrations were prepared in the cuvette, with the stock solution of Example 2 in the bulbs. After measurements were made on the cuvette solution, the stock solution in the bulb was mixed with the cuvette solution, diluting the concentration by half. Luminescence lifetime measurements were taken. The data measurements are reported in Table 2, below and in FIG. 1, which is a Stem-Volmer plot of $k_{obs}$ vs. concentration of DCQ indicating oxidative quenching of the compound prepared according to Example 2 with 2,6-dibenzoquinone (Q). In FIG. 1, y=9.043×10$^9$(x)+36767 and R$^2$=0.9997. The data is consistent with diffusion-limited electron transfer, with a rate constant of k=9.04×10$^9$ M$^{-1}$s$^{-1}$.

TABLE 2

Data for Excited State Lifetime Measurements.

| Concentration of DCQ | $k_{obs}$ (s$^{-1}$) | Lifetime ($\tau$, 1/$k_{obs}$) ($\mu$s) |
|---|---|---|
| 0 $\mu$M | 4.70 × 10$^4$ | 21.26 |
| 11.3 $\mu$M | 1.34 × 10$^5$ | 7.48 |
| 22.6 $\mu$M | 2.25 × 10$^5$ | 4.44 |
| 33.8 $\mu$M | 3.51 × 10$^5$ | 2.84 |
| 42.4 $\mu$M | 4.29 × 10$^5$ | 2.33 |
| 68.7 $\mu$M | 6.65 × 10$^5$ | 1.50 |
| 84.7 $\mu$M | 7.84 × 10$^5$ | 1.27 |
| 169.5 $\mu$M | 1.57 × 10$^6$ | 0.635 |

Quantum Yield Experiments

Emission spectra were recorded on a Spex Fluorolog-2 spectro-fluorometer. A solution of analyte or reference compound in benzene, diethyl ether, tetrahydrofuran, or acetonitrile was prepared in a nitrogen filled glovebox. Cuvettes (1 cm path length) were charged with this solution and sealed with a teflon stopper. The absorption spectra were acquired both before and after fluorescence measurements to ensure the sample was not degrading. In some cases, a very minor amount (<1%) of photodecomposition was observed, with more pronounced degradation under prolonged exposure to light. Fluorescence measurements were performed at the specified wavelength and corrected for detector response after equilibration to 298 K. The area under the curve of the emission spectrum was determined using standard trapezoidal integration methods. Quantum yields were then calculated by known methods using Equation I, below. The results are reported in Table 3, below. Quinine sulfate in 0.1 N H$_2$SO$_4$[3] ($\phi$=0.54) and [Ru(bpy)$_3$][PF$_6$] in acetonitrile ($\phi$=0.075) were used as reference standards.

$$\phi = (QR)(I/IR)(ODR/OD)(\eta^2/\eta_R^2) \qquad \text{Equation I}$$

In Equation 1, $\phi$ is the quantum yield of the sample, QR is the quantum yield of the reference, I is the integrated intensity of the analyte, IR is the integrated intensity of the reference, ODR is the optical density of the reference in absorption units, OD is the optical density of the analyte in absorption units, $\eta$ is the index of refraction of the solvent in which the analyte was dissolved, and $\eta_R$ is the index of refraction of the solvent in which the reference was dissolved.

Lithium salts of the ligands were prone to photodecomposition. Specifically, the compounds prepared according to Examples 1 (decomposed by 10%), 5 (decomposed by 20%) and 6 (decomposed by 15%) all decomposed significantly after irradiation in the fluorimeter. The quantum yield results reported below are crude values, and are reported with confidence of ±5 on the last significant figure for measurements in benzene, and ±10 on the last two significant figures for measurements in Et$_2$O and THF.

TABLE 3

Data for Quantum Yield Measurements.

| Sample (solvent) | $\lambda_{ex}$ | $\phi^a$ |
|---|---|---|
| Example 1 (Et$_2$O) | 430 | 0.16 |
| Example 2 (C$_6$H$_6$) | 430 | 0.56 |
| | 350 | 0.52 |
| Example 2 (Et$_2$O) | 430 | 0.29 |
| Example 2 (THF) | 430 | 0.27 |
| Example 3 (C$_6$H$_6$) | 430 | 0.21 |
| | 350 | 0.17 |
| Example 3 (Et$_2$O) | 430 | 0.10 |
| Example 3 (THF) | 430 | 0.05 |
| Example 4 (C$_6$H$_6$) | 430 | 0.31 |
| | 350 | 0.36 |
| Example 4 (Et$_2$O) | 430 | 0.15 |
| Example 4 (THF) | 430 | 0.05 |
| Example 5 (Et$_2$O) | 430 | 0.12 |
| Example 6 (Et$_2$O) | 430 | 0.05 |
| Example 7 (C$_6$H$_6$) | 430 | 0.70 |
| Example 7 (Et$_2$O) | 430 | 0.55 |
| Example 7 (THF) | 430 | 0.30 |
| Example 8 (C$_6$H$_6$) | 430 | 0.16 |
| Example 8 (Et$_2$O) | 430 | 0.08 |
| Example 8 (THF) | 430 | 0.07 |
| Example 9 (C$_6$H$_6$) | 430 | 0.00106 |
| Example 10 (C$_6$H$_6$) | 350 | 0.088 |

Photophysical Properties

The following Table 4 reports certain photophysical properties of the compounds prepared according to Examples 1 through 10. In Table 4, $\lambda$ (cm$^{-1}$) is the reorganization energy, and is calculated according to Equation 2, below.

$$\lambda = (\Delta v_{1/2})^2/(16RT \ln 2) \qquad \text{Equation 2}$$

In Equation 2, $\Delta v_{1/2}$ is the full width at half maximum, R is 8.31451 J/mol·K, and T is 298 K.

Results

Figure 2:
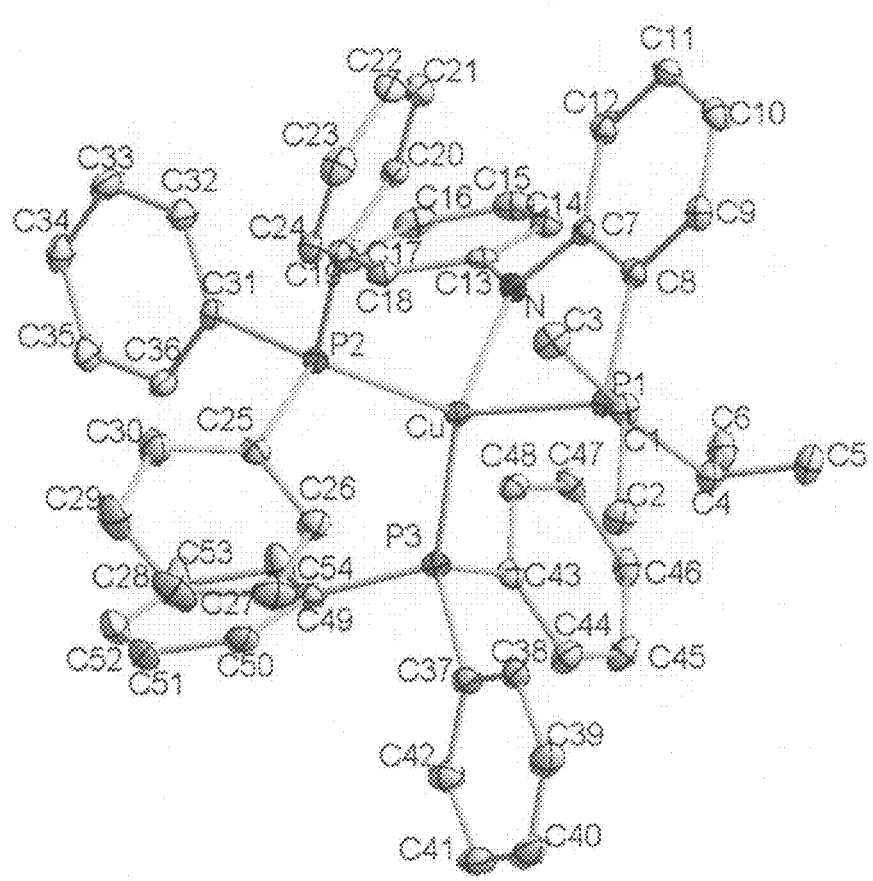
FIG. 2 is the molecular structure of the complex prepared according to Example 2 with hydrogen atoms omitted for clarity.
Figure 3A:
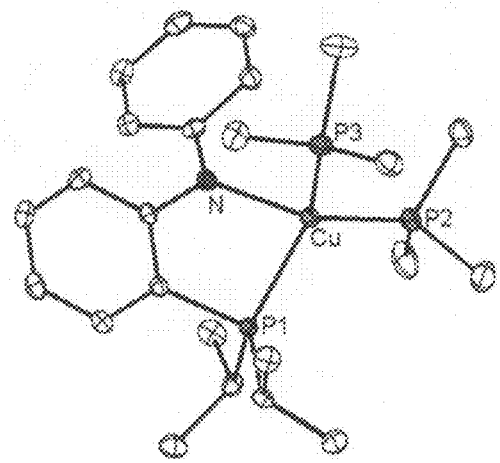
FIG. 3A is the molecular structure of the complex prepared according to Example 3 with hydrogen atoms omitted for clarity.
Figure 4:
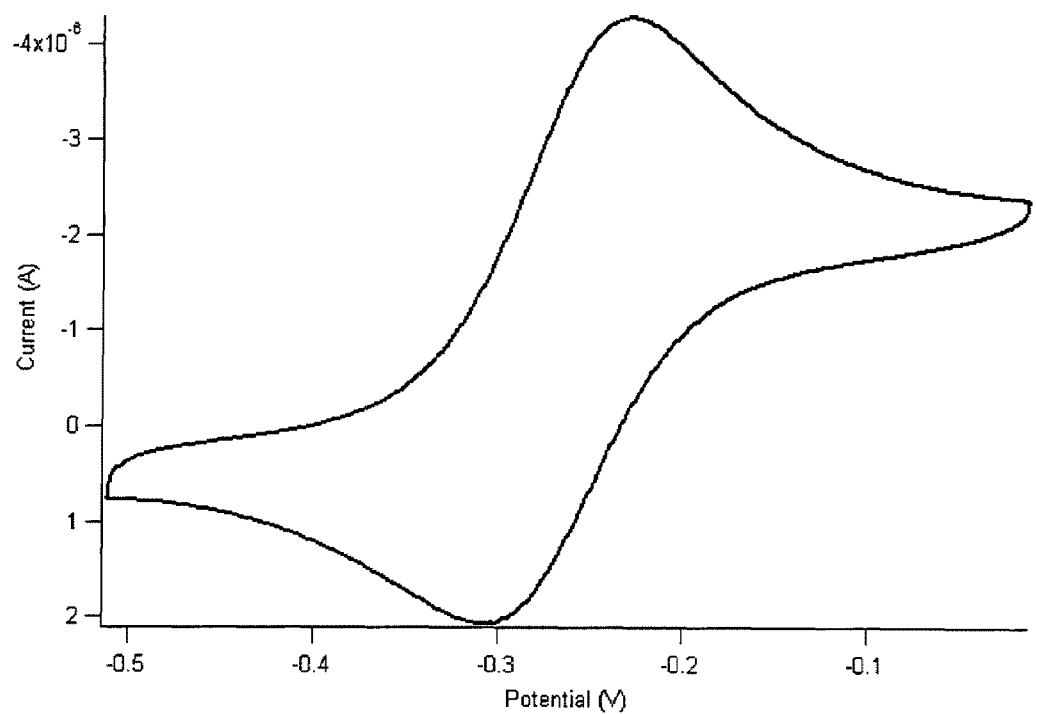
FIG. 4 is a cyclic voltammogram of the complex prepared according to Example 2.

X-ray diffraction analysis of the complexes prepared according to Examples 2, 3 and 4 confirm that the complexes have monomeric, pseudotetrahedral structures. FIG. 2 shows the structure of the complex prepared according to Example 2, and FIG. 3A shows the structure of the complex prepared according to Example 3. Cyclic voltammetry of the complex of Example 2 shows a reversible peak at −270 mV vs. Fc/Fc+ (See FIG. 4). The X-ray diffraction analysis of the complex prepared according to Example 4 confirmed an overall connectivity relate to the complexes prepared according to Examples 2 and 3. However, the structure of the complex of Example 4 suffered from twinning.

Figure 5:
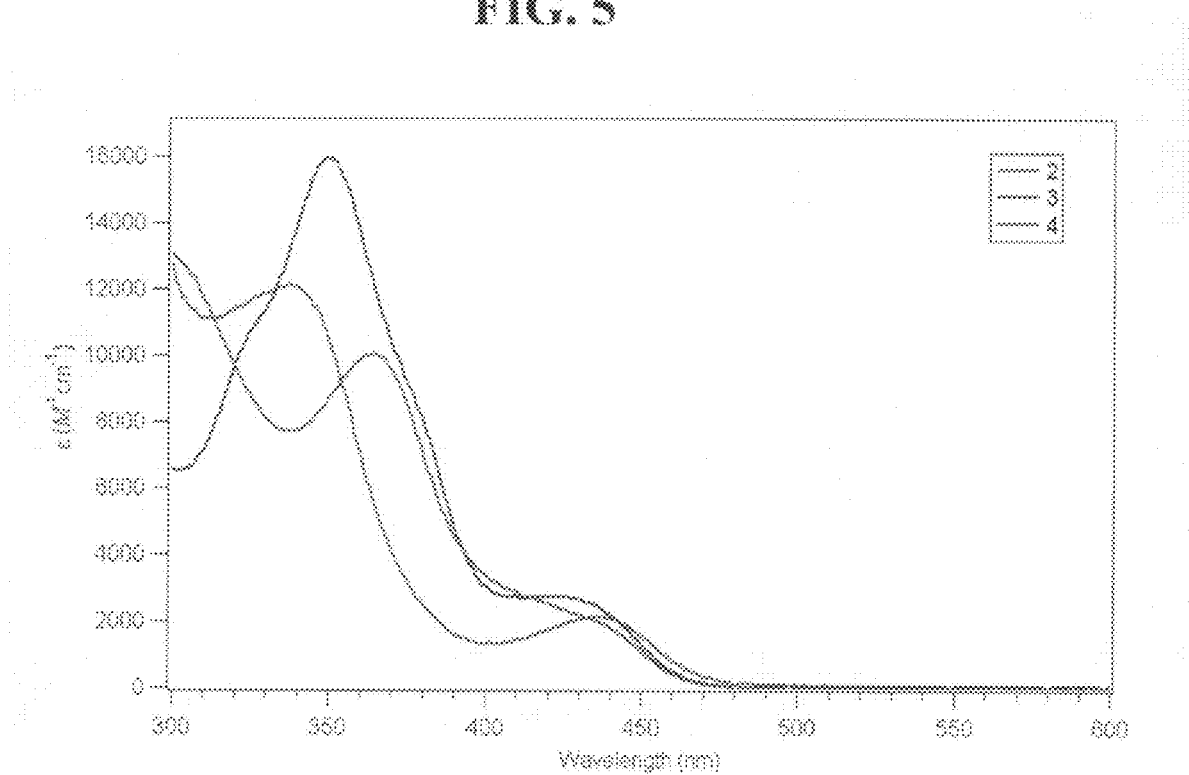
FIG. 5 is an overlay of absorption spectra of the complexes prepared according to Examples 2, 3 and 4.
Figure 5A:
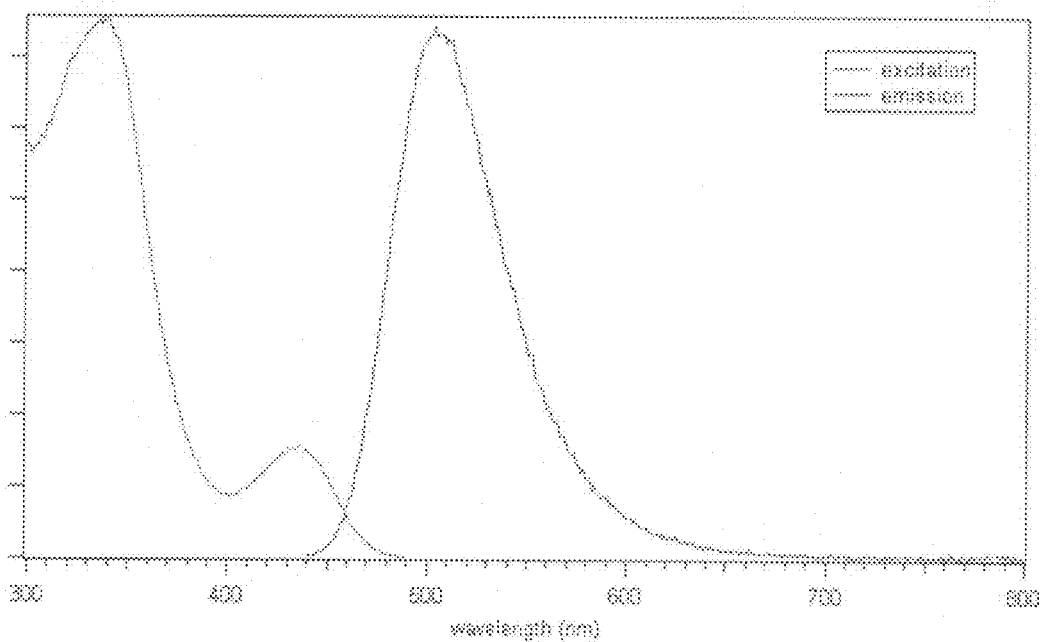
FIG. 5A depicts emission/excitation spectra of the complex prepared according to Example 2 ($\lambda_{ex}$=430 nm)
Figure 5B:
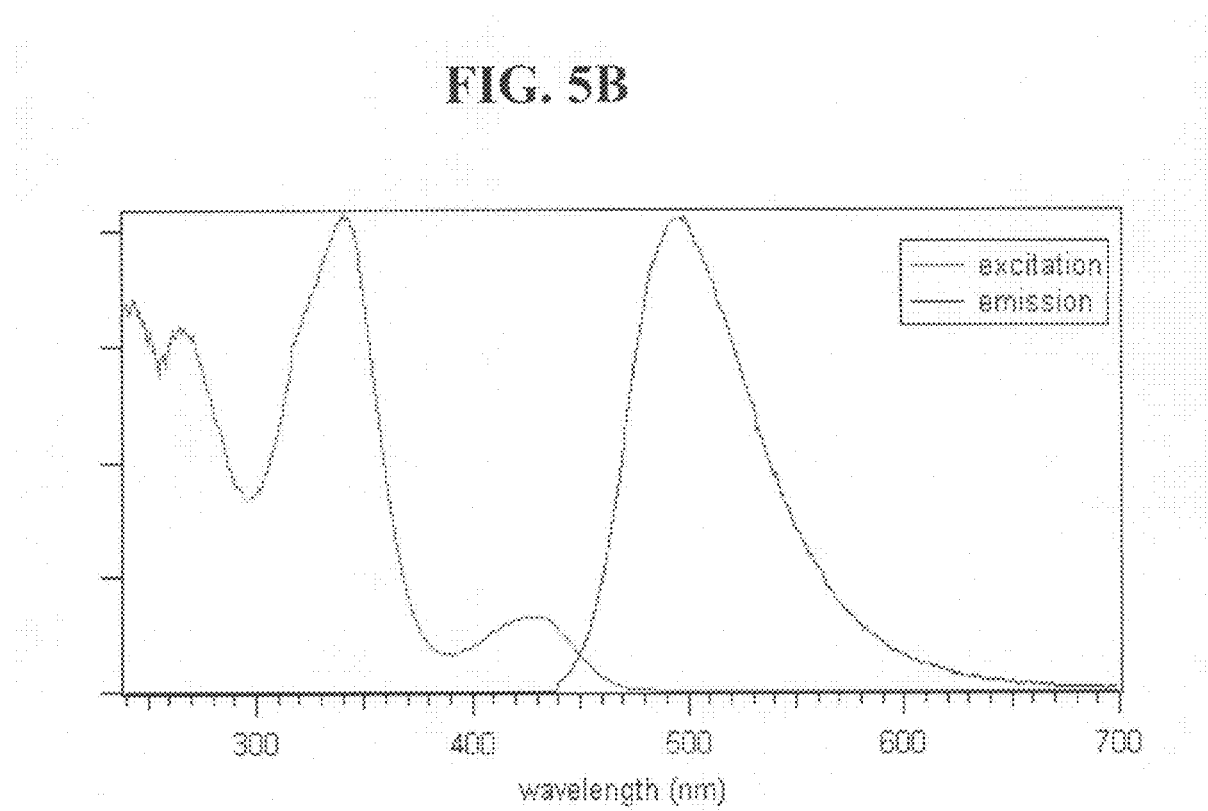
FIG. 5B depicts emission/excitation spectra of the complex prepared according to Example 3 ($\lambda_{ex}$=430 nm)
Figure 5C:
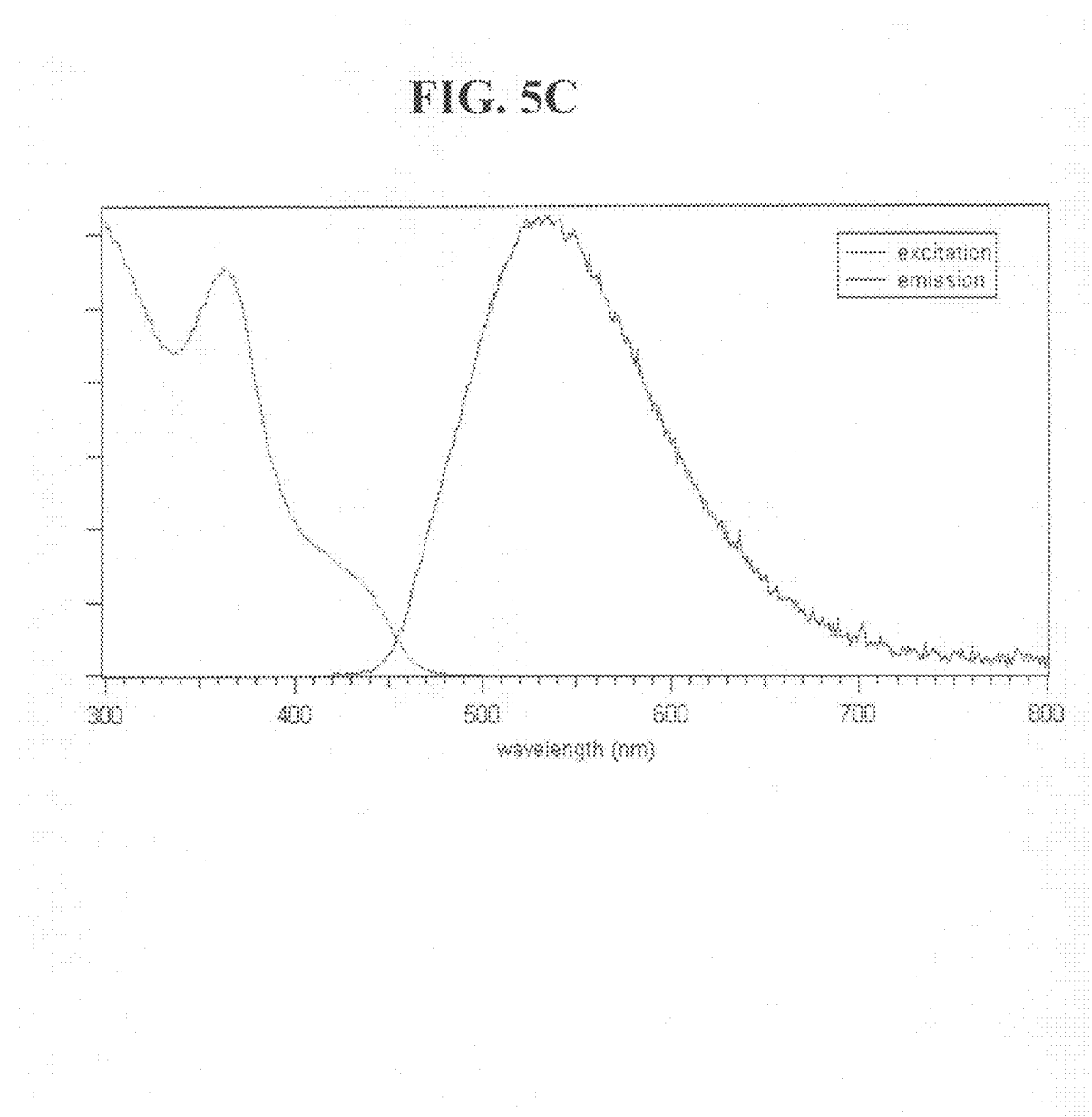
FIG. 5C depicts emission/excitation spectra of the complex prepared according to Example 4 ($\lambda_{ex}$=430 nm)

Absorption spectra for the complexes prepared according to Examples 2, 3 and 4 (shown in FIG. 5) feature similar peaks around 430 nm ($\epsilon$=2,000-2,500 M−1 cm−1) and 350 nm ($\epsilon$=10,000 M−1 cm−1), along with more complicated higher energy transitions. The complexes prepared according to Examples 2, 3 and 4 glow bright green under visible light, both in the solid state and in solution. Excitation into any absorption band leads to sharp, featureless emission peaks at 298K, i.e. 504 nm for the complex of Example 2, 497 for the complex of Example 3, and 534 nm for the complex of Example 4 (see FIG. 6). The quantum efficiency of each complex in benzene solution at 298K was assessed with excitation at 430 nm and 350 nm. The emission/excitation spectra for the complexes of Examples 2, 3 and 4 are shown in FIGS. 5A, 5B and 5C, respectively.

As shown in the following Table 4, quantum yields of the complexes vary widely depending on the auxiliary ligand, from $\Phi$=0.56 for the complex of Example 2, to $\Phi$=0.21 for the complex of Example 3. Such high solution quantum efficiency is unique among monomeric Cu systems, as highlighted by the results listed in Table 4. When more polar solvents, such as diethyl ether or THF are employed, the luminescence efficiency is significantly attenuated, typically by about 50%.

The complexes of Examples 2, 3 and 4 show long luminescence lifetimes in benzene solutions, i.e. 20.2(1) μs for Example 2 (see FIG. 6), 22.3(7) μs for Example 3, and 16.3(3) μs for Example 4. The lifetimes in Et2O were virtually identical to those in benzene. The luminescence decay of the complex of Example 3 ($PME_3$ adduct) has two components, with a small spike indicating the decay of a shorter-lived species (<10 ns; see Table 1 above).

Figure 6:
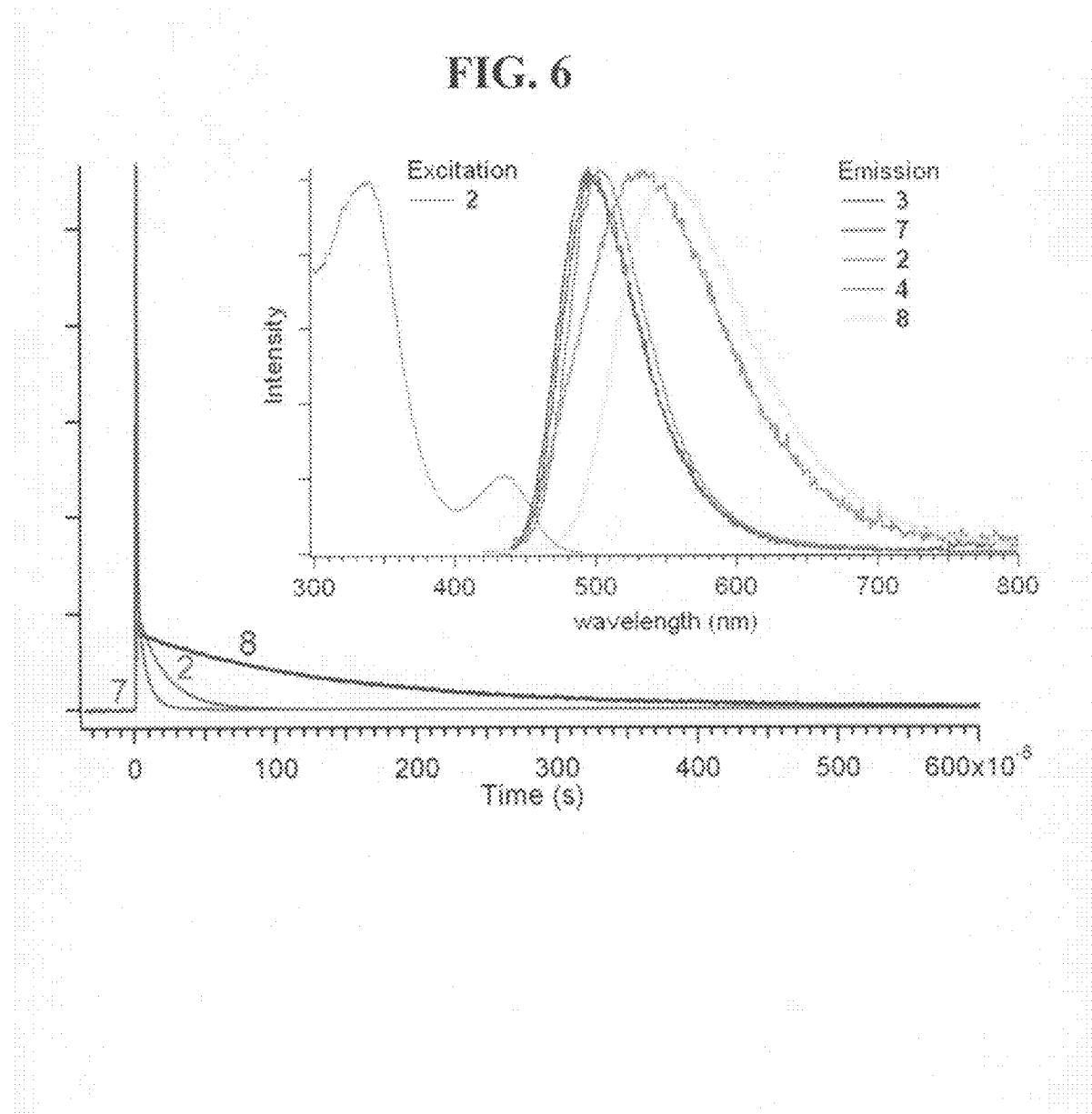
FIG. 6 depicts luminescence decay traces of the complexes prepared according to Examples 7 (green), 2 (red) and 8 (blue), and an excitation spectrum of the complex prepared according to Example 2 (inset) and normalized emission spectra.
Figure 7:
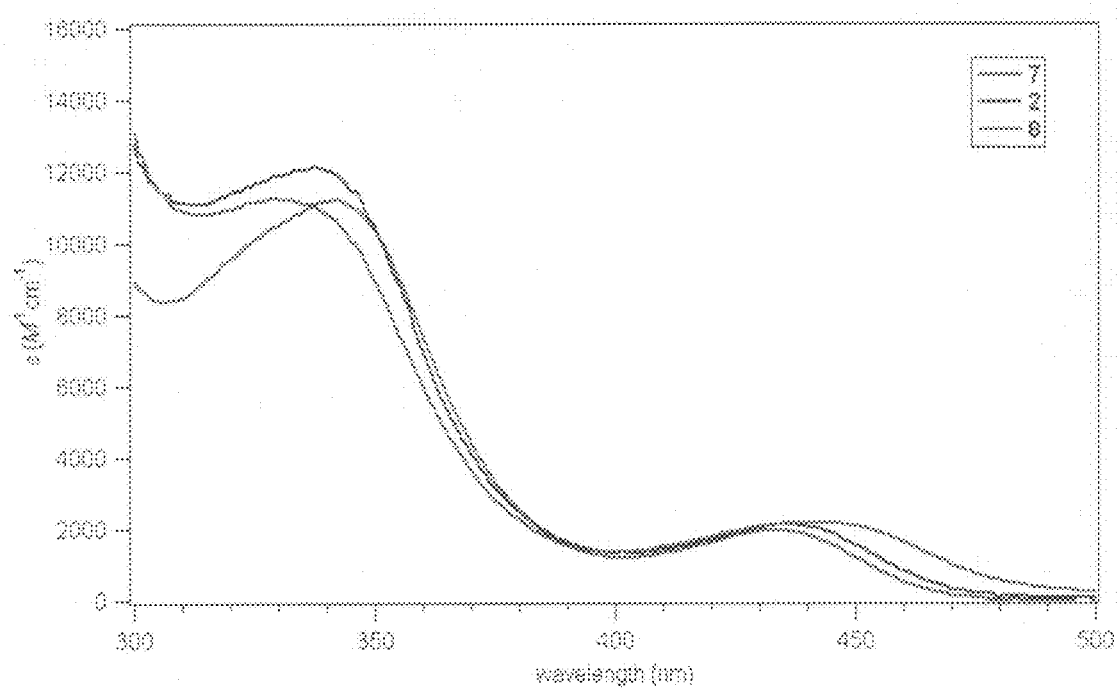
FIG. 7 is an overlay of absorption spectra of the complexes prepared according to Examples 2, 7 and 8.
Figure 7A:
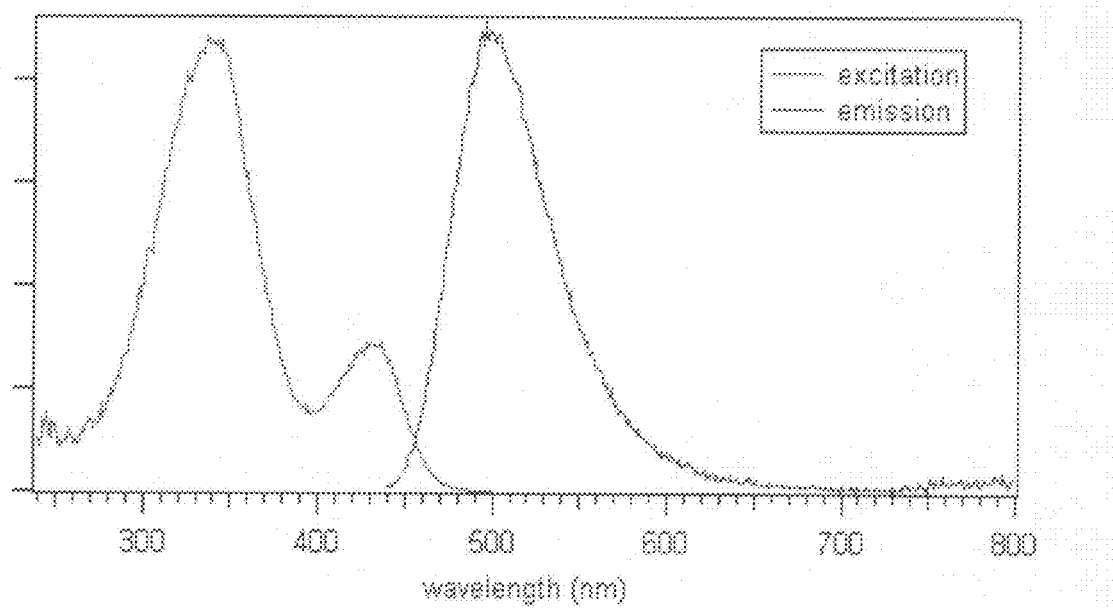
FIG. 7A depicts emission/excitation spectra of the complexes prepared according to Example 7 (λ=430 nm)

In Examples 5 and 6, two PN ligands with donating and withdrawing groups on the arene backbone were used to tune the emission frequency. The complexes of Examples 5 (methyl substituted [$^{Me}$PN]Li) and 6 ($CF_3$ substituted [$^{CF3}$PN]Li) were prepared analogously to the complex of Example 1, with subsequent metalation in the present of 2 equivalents of PPh3, yielding [$^{Me}$PN]Cu(PPh$_3$)$_2$ according to Example 7, and [$^{CF3}$PN]Cu(PPh$_3$)$_2$ according to Example 8. As shown in FIG. 7, methyl-substitution does not generally perturb the optical spectrum when compared with the complex of Example 2, and only a 6 nm blue-shift is observed for its emission maximum (as shown in FIG. 6). The complex according to Example 7 emits significantly brighter than that of the complex of Example 2, with $\Phi$=0.70, and a concomitantly shorter luminescence lifetime of 6.7(1) μs. The emission/excitation spectra of the complex of Example 7 is shown in FIG. 7A.

Figure 8:
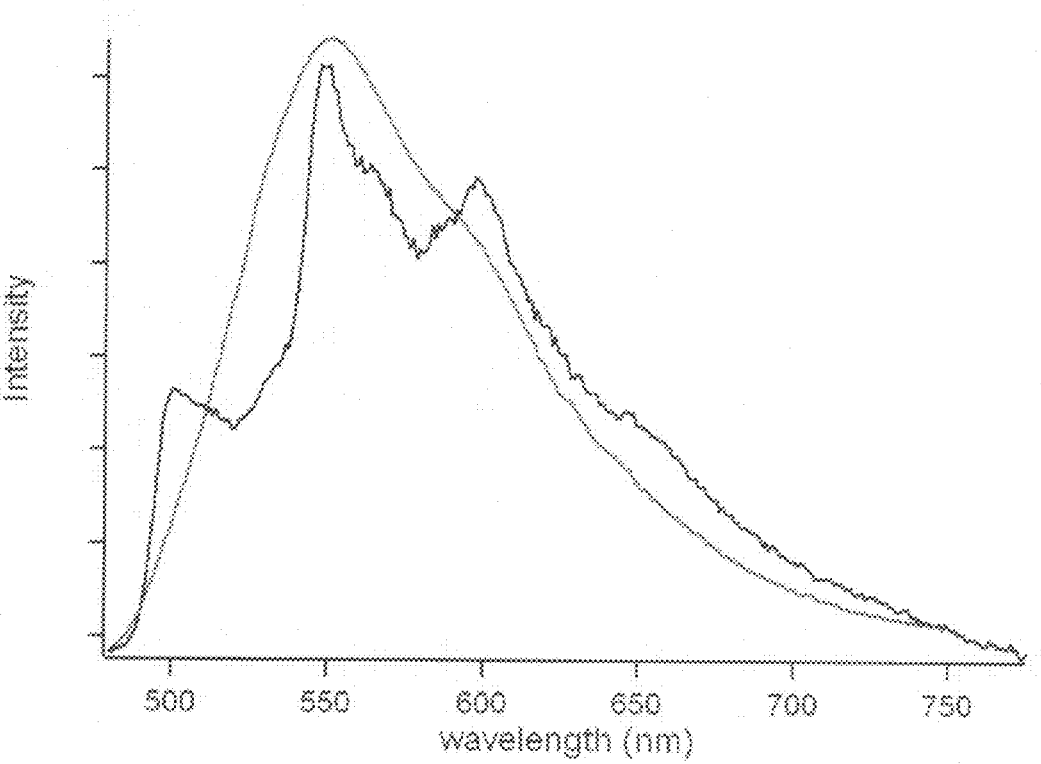
FIG. 8 depicts emission spectra of a polycrystalline complex prepared according to Example 8 ($\lambda_{ex}$=430 nm) at 77 K (black) and 298K (red)

As shown in FIG. 7, relative to the complex of Example 2, $CF_3$-substitution on the ligand backbone imparts a 10 nm red-shift in the optical spectrum ($\lambda_{max}$=444 nm) for the complex of Example 8, which is matched by a 48 nm red-shift in the emission maximum (see FIG. 6). The quantum efficiency of the complex of Example 8 in benzene at 298K, with $\Phi$=0.16, presents a substantial decrease compared to the complexes of Examples 2 and 7 (PPh$_3$ adducts). As shown in FIG. 8, the polycrystalline complex of Example 8 displays structured emission at 77 K, and broad emission at 298 K that closely resembles the room temperature solution data. The similar emission from crystalline and solution samples is consistent with an unchanged structure in solution. However, there is a dramatic increase in the measured luminescence

TABLE 4

Photophysical Comparison of Cu Complexes at 298K

| Complex | Solvent | $\lambda_{abs}$ (nm) | $\lambda_{em}$ (nm) | $\phi_{em}{}^a$ | $\tau$ (μs) |
|---|---|---|---|---|---|
| Example 1 | Et$_2$O | 411 | 480 | 0.16 | 0.012(1) |
| Example 2 | C$_6$H$_6$ | 434 | 504 | 0.56 | 20.2(1) |
| Example 3 | C$_6$H$_6$ | 427 | 497 | 0.21 | 22.3(7) |
| Example 4 | C$_6$H$_6$ | 423 | 534 | 0.32 | 16.3(3) |
| Example 7 | C$_6$H$_6$ | 433 | 498 | 0.70 | 6.7(1) |
| Example 8 | C$_6$H$_6$ | 444 | 552 | 0.16 | 150(3) |
| [dbpCuPOP]+ (dbp = 2,9-di-n-butyl-1,10-phenanthroline; POP = bis[2-(diphenylphosphino)phenyl] ether) | CH$_2$Cl$_2$ | 378 | 560 | 0.16 | 16.1[7] |
| [dmpCudppe]+ (dmp = 2,9-dimethyl-1,10-phenanthroline) | CH$_2$Cl$_2$ | 400 | 630 | 0.010 | 1.33[7] |
| CuI(dppb)PPh$_3$ (dppb = 1,2-bis[diphenylphosphino] benzene) | Me-THF | ~380 | 550 | 0.01 | <1[Error! Bookmark not defined.] |

Figure 7B:
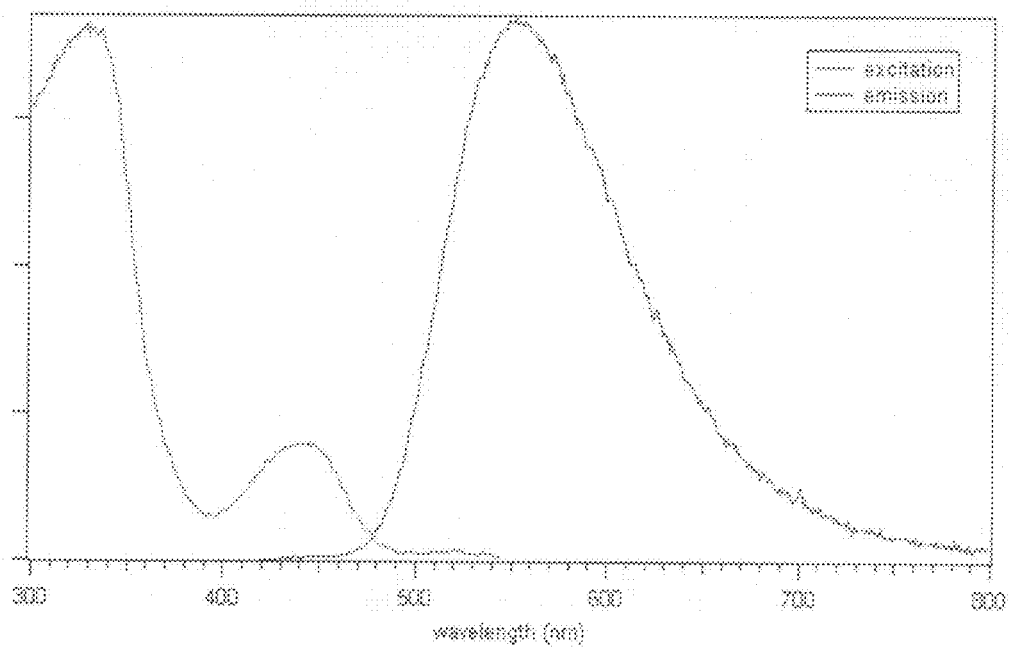
FIG. 7B depicts emission/excitation spectra of the complexes prepared according to Example 8 ($\lambda_{ex}$=430 nm)

$^a$ = quantum yields are reported with a confidence of ±5 on the last significant figure;
b = data reported in CH2Cl2;
c = data reported in 2-methyl-tetrahydrofuran lifetime, to 150(3) μs (see FIG. 6). As for the complex of Example 3 (PME₃ adduct), there is a two-component decay profile, with a much more pronounced short-lived (<10 ns) species. These decay profiles reflect independent singlet/triplet emission pathways. The triplet excited state species is nearly an order of magnitude longer-lived than dbpCu(POP), and may be the longest-lived monomeric Cu emitter presently known in solution at ambient temperature. The emission/excitation spectra of the complex of Example 8 is shown in FIG. 7B.

Figure 3B:
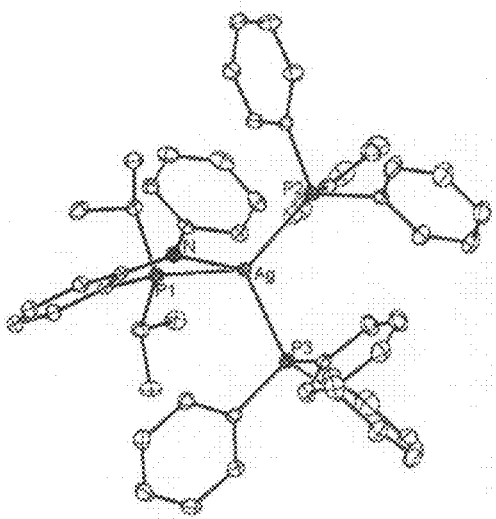
FIG. 3B is the molecular structure of the complex prepared according to Example 9 with hydrogen atoms omitted for clarity.

The complex of Example 9 ([PN]Ag(PPh₃)₂) was prepared by adding the complex of Example 1 to AgOTF in the presence 2 equivalents of PPh3 in diethyl ether, affording a golden yellow complex. X-ray diffraction analysis of the resulting product showed an analogous geometry to the copper complex of Example 2 (see FIG. 3B). The complex of Example 9 is a rare example of a mononuclear silver amide complex. While its absorption spectrum (shown in FIG. 9) is similar to those of the complexes of Examples 2 and 3, its emission spectrum (shown in FIG. 10) exhibits a much broader peak at 544 nm, suggesting loss of energy via structural reorganization. The luminescence is attenuated relative to the corresponding Cu complexes (Φ=0.0010), and it has a lifetime that is likewise much shorter (125(5) ns).

Figure 9:
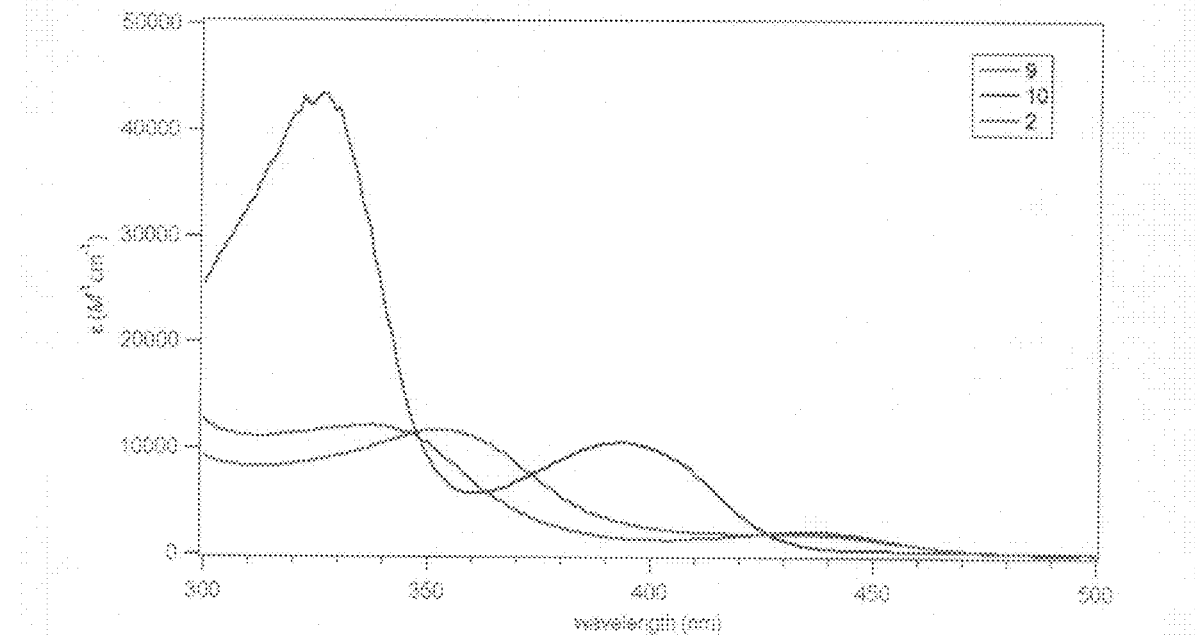
FIG. 9 is an overlay of absorption spectra of the complexes prepared according to Examples 2, 9 and 10.
Figure 10:
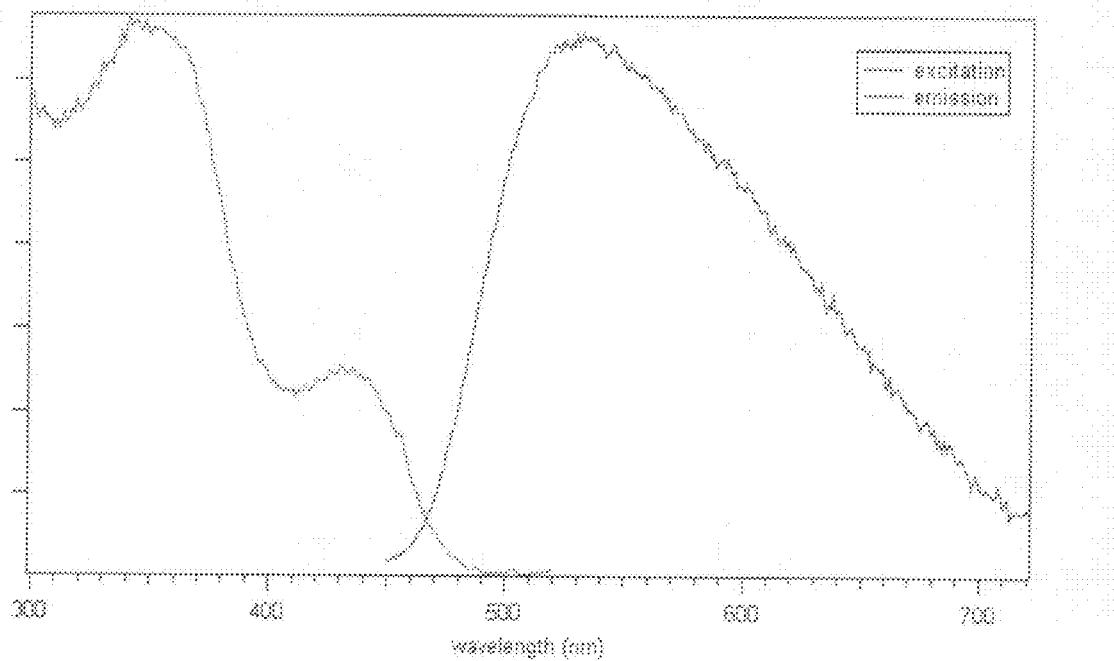
FIG. 10 depicts emission/excitation spectra of the complex prepared according to Example 9 ($\lambda_{ex}$=430 nm)
Figure 11:
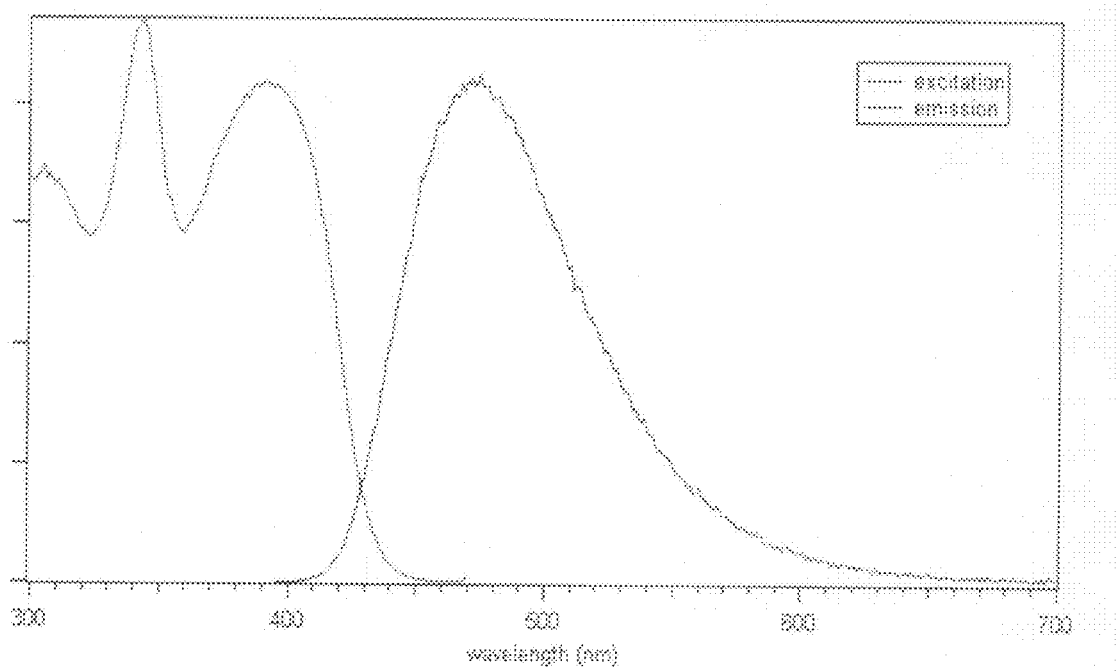
FIG. 11 depicts emission/excitation spectra of the complex prepared according to Example 10 ($\lambda_{ex}$=350 nm)

Metathesis of two equivalents of the complex of Example 1 with ZnCl2, followed by filtration and crystallization according to Example 10, provided yellow [PN]₂Zn. Excitation at either absorption feature (λmax=324 nm, 390 nm) led to aquamarine blue emission centered at 475 nm that was substantially less efficient and shorter lived than for the Cu complexes (Φ=0.088; τ<10 ns). The absorption spectrum of the [PN]₂Zn complex prepared according to Example 10 is shown in FIG. 9, and the excitation/emission spectra are shown in FIG. 11.

Figure 3C:
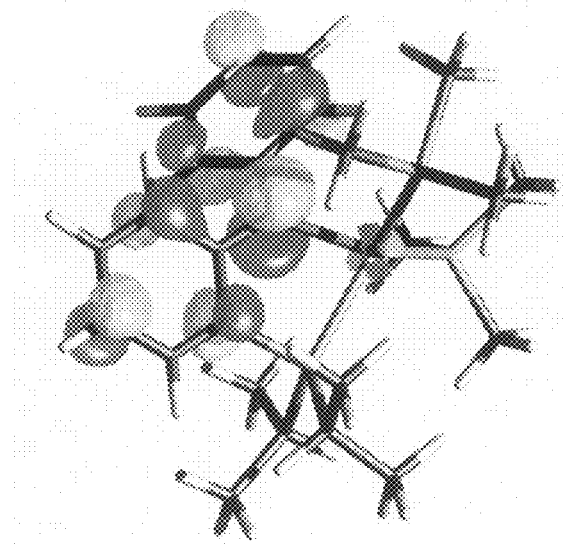
FIG. 3C is a depiction of the highest occupied molecular orbital (HOMO) of the complex prepared according to Example 3 as determined by discrete Fourier transform (DFT)
Figure 3D:
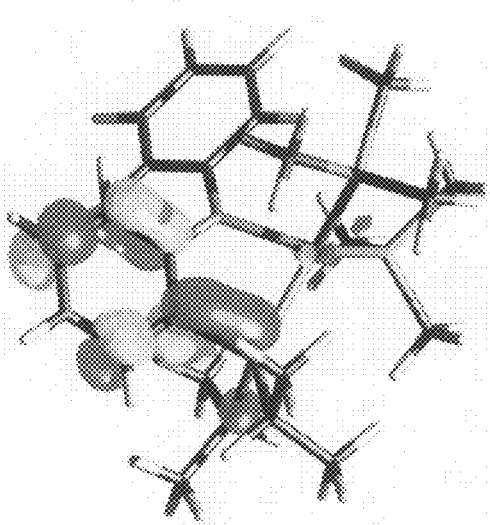
FIG. 3D is a depiction of the lowest unoccupied molecular orbital (LUMO) of the complex prepared according to Example 3 as determined by DFT.

Although the silver and zinc complexes exhibit useful luminescence properties, the use of copper enables access to the long-lived triplet excited state. Also, in the absence of Cu, only fluorescence is observed. An intraligand charge transfer (ILCT) transition may be present in all of the compounds prepared according to Examples 1 through 10. Excitation from the N lone pair to arene π* is consistent with the calculated HOMO and LUMO of the compound of Example 3, where substantial N lone pair character (mixed with non-bonding arene π character) is present in the HOMO, and a predominantly π* orbital is depicted in the LUMO (the HOMO and LUMO of the compound of Example 3 are shown in FIGS. 3C and 3D respectively). Emission from this transition is manifested as short-lived fluorescence for the non-copper-containing species of Examples 1, 5, 6 and 10. However, the Cu emitters of Examples 2, 3, 4, 7 and 8 seem to display both singlet and triplet emissions, indicative of additional luminescence properties.

Figure 12:
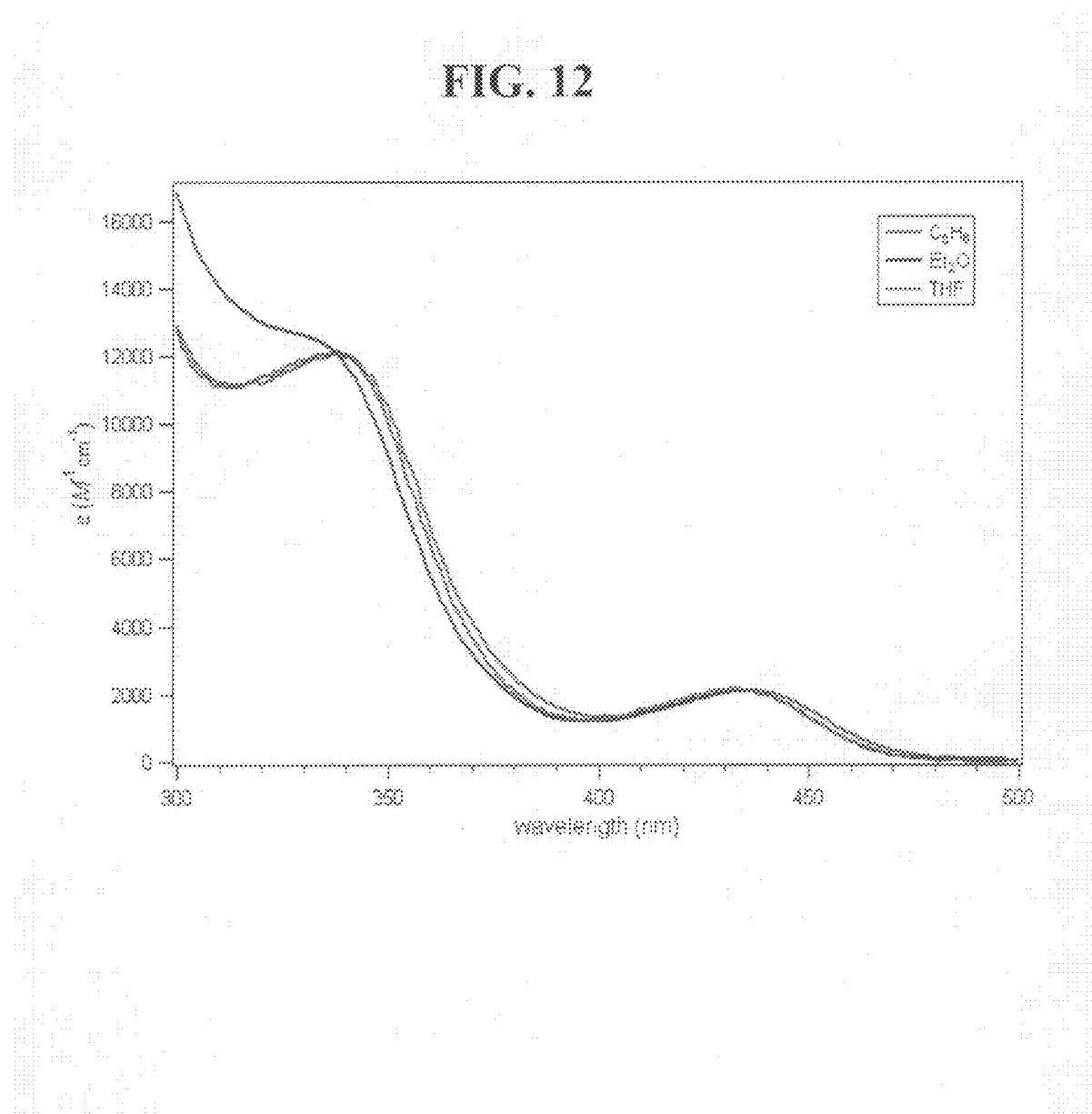
FIG. 12 is an overlay of optical spectra of the complex prepared according to Example 2 in benzene, diethyl ether, and THF.

Although one description of the observed Cu phosphorescence is metal-to-ligand charge transfer (MLCT) from a Cu d-orbital to the arene π* orbital, this description is inconsistent with the data. First, as shown in FIG. 9, only minor differences are observed in the absorption spectra of Cu and Ag complexes of Examples 2 and 9, respectively, rather than the often striking shift in MLCT transition energy caused by moving to a 4d element. Second, there is minimal solvent dependence on the ground state absorption spectrum of the complex of Example 2, as shown in FIG. 12, while significant solvent dependence is often observed in well-defined MLCT systems. Third, MLCT states generally have large Stokes shifts, but the complexes here all have anomalously small Stokes shifts for MLCT. Finally, the Cu complexes do not appear to be quenched by a five-coordinate exciplex, as is typical for MLCT. If exciplex quenching played a significant role, the differences in steric bulk between the compound of Examples 2, 3 and 4 might be expected to have a more significant effect on the phosphorescence lifetime. Electronic effects seem to play a more important role when comparing the compound of Examples 2, 7 and 8, as the sterically similar (but electronically diverse) complexes have quite different lifetimes and quantum efficiencies. Given this data, the Cu phosphorescence appears to be derived from good orbital overlap and energetic matching between the Cu d-manifold and the ligand π* system, which allows facile intersystem crossing to a Cu-stabilized triplet.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A monomeric metal complex comprising a compound represented by Formula 1:

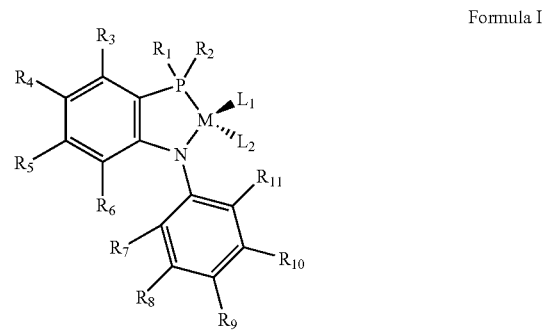

Formula I wherein:
M is a d¹⁰ metal;
each of $R_1$ and $R_2$ is a substituted or unsubstituted hydrocarbon substituent;
each of $R_3$ through $R_{11}$ is independently selected from the group consisting of hydrogen, halogens, hydroxyl groups, cyano groups and substituted and unsubstituted hydrocarbon substituents, wherein $R_6$ and $R_7$ may optionally combine to form a single bond; and
each of $L_1$ and $L_2$ is selected from the group consisting of substituents represented by $PX_3$, wherein X is a hydrocarbon substituent, wherein $L_1$ and $L_2$ may optionally combine to form a single ligand.

2. A monomeric metal complex according to claim 1, wherein M is selected from the group consisting of Cu, Ag and Zn.

3. A monomeric metal complex according to claim 1, wherein M is Cu.

4. A monomeric metal complex according to claim 1, wherein each of $R_1$ and $R_2$ is independently selected from the group consisting of substituted and unsubstituted alkyl groups, substituted and unsubstituted alkenyl groups, substituted and unsubstituted alkynyl groups, substituted and unsubstituted aryl groups, and substituted and unsubstituted heteroaryl groups.

5. A monomeric metal complex according to claim 4, wherein $R_1$ and $R_2$ are both isopropyl groups.

6. A monomeric metal complex according to claim 4, wherein $R_1$ and $R_2$ are both phenyl groups.

7. A monomeric metal complex according to claim 1, wherein each of $R_3$ through $R_{11}$ is independently selected from the group consisting of hydrogen, halogens, hydroxyl groups, cyano groups, alkoxy groups, acyl groups, substituted and unsubstituted alkyl groups, substituted and unsubstituted alkenyl groups, substituted and unsubstituted alkynyl groups, substituted and unsubstituted aryl groups, and substituted and unsubstituted heteroaryl groups.

8. A monomeric metal complex according to claim 7, wherein at least one of $R_3$ through $R_{11}$ is not hydrogen.

9. A monomeric metal complex according to claim 7, wherein at least $R_5$ is not hydrogen.

10. A monomeric metal complex according to claim 1, wherein one of $R_3$ through $R_6$ and one of $R_7$ through $R_{11}$ form a single bond.

11. A monomeric metal complex according to claim 10, wherein $R_6$ and $R_7$ form the single bond to form a compound represented by Formla 3:

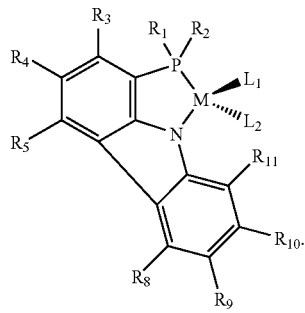

Formula 3

12. A monomeric metal complex according to claim 1, wherein each of $L_1$ and $L_2$ is selected from the group consisting of $P(CH_3)_3$ and $P(C_6H_5)_3$.

13. A monomeric metal complex according to claim 1, wherein $L_1$ and $L_2$ comprise a single amidophospine ligand to form a compound represented by Formula 6A:

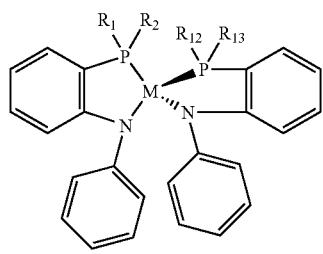

Formula 6A wherein each of $R_{12}$ and $R_{13}$ is substituted or unsubstituted hydrocarbon substituent.

14. A monomeric metal complex according to claim 1, wherein $L_1$ and $L_2$ comprise a single 1,2-(diisopropylphosphino)ethane ligand to form a compound represented by Formula 6B:

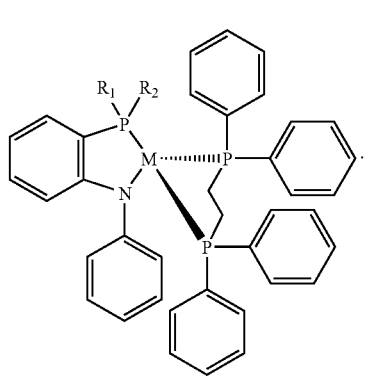

Formula 6B

15. A monomeric metal complex comprising a compound represented by Formula 1:

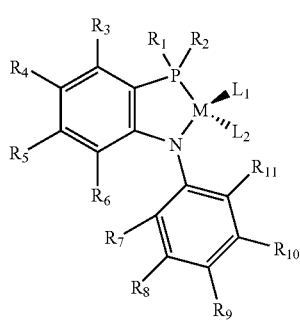

Formula I wherein:
M is selected from the group consisting of Cu, Ag and Zn;
each of $R_1$ and $R_2$ is selected from the group consisting of substituted and unsubstituted alkyl groups, substituted and unsubstituted alkenyl groups, substituted and unsubstituted alkynyl groups, substituted and unsubstituted aryl groups, and substituted and unsubstituted heteroaryl groups;
each of $R_3$ through $R_{11}$ is selected from the group consisting of hydrogen, halogens, hydroxyl groups, cyano groups, alkoxy groups, acyl groups, substituted and unsubstituted alkyl groups, substituted and unsubstituted alkenyl groups, substituted and unsubstituted alkynyl groups, substituted and unsubstituted aryl groups, and substituted and unsubstituted heteroaryl groups; and wherein $R_6$ and $R_7$ may optionally combine to form a single bond; and
each of $L_1$ and $L_2$ is selected from the group consisting of substituents represented by $PX_3$, wherein X is selected from the group consisting of alkyl groups, alkenyl groups, alkynyl groups, aryl groups and heteroaryl groups wherein $L_1$ and $L_2$ may optionally combine to form a single ligand.

16. A monomeric metal complex according to claim 15, wherein at least $R_5$ is not hydrogen.

17. A monomeric metal complex according to claim 15, wherein $R_6$ and $R_7$ form a single bond to form a compound represented by Formula 3:

Formula 3

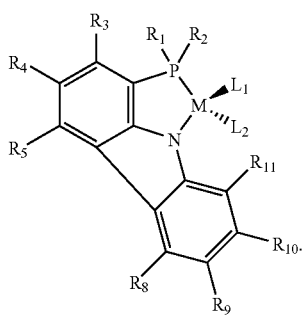

18. A monomeric metal complex according to claim 15, wherein $L_1$ and $L_2$ comprise a single amidophosphine ligand to form a compound represented by Formula 6A:

Formula 6A

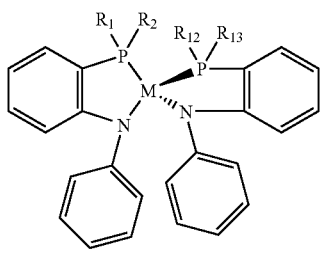

wherein each of $R_{12}$ and $R_{13}$ is a substituted or unsubstituted hydrocarbon substituent.

19. A monomeric metal complex according to claim 15, wherein $L_1$ and $L_2$ comprise a single 1,2-(diisopropylphosphino)ethane ligand to form a compound represented by Formula 6B:

Formula 6B

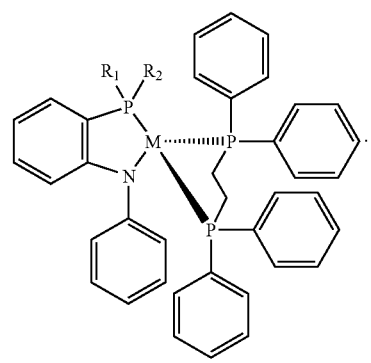

20. A monomeric metal complex according to claim 14, wherein M is Cu.

* * * * *

UNITED STATES PATENT AND TRADEMARK OFFICE
CERTIFICATE OF CORRECTION

PATENT NO. : 7,683,183 B2
APPLICATION NO. : 11/888210
DATED : March 23, 2010
INVENTOR(S) : Jonas C. Peters Page 1 of 1

It is certified that error appears in the above-identified patent and that said Letters Patent is hereby corrected as shown below:

| | |
|---|---|
| Column 23, Claim 11, line 18 | Delete "formla" Insert -- formula -- |
| Column 23, Claim 13, line 61 | After "is" Insert -- a -- |
| Column 24, Claim 15, line 52 | Delete "groups;" Insert -- groups, -- |
| Column 24, Claim 15, line 59 | Insert after "groups" -- , -- |

Signed and Sealed this

Sixteenth Day of November, 2010

David J. Kappos
*Director of the United States Patent and Trademark Office*